United States Patent [19]
Thaisrivongs

[11] Patent Number: 4,864,017
[45] Date of Patent: Sep. 5, 1989

[54] NOVEL RENIN INHIBITING PEPTIDES HAVING A DIHYROXYETHYLENE ISOSTERE TRANSITION STATE INSERT

[75] Inventor: Suvit Thaisrivongs, Portage, Mich.

[73] Assignee: The Upjohn Company, Kalmazoo, Mich.

[21] Appl. No.: 235,860

[22] Filed: Aug. 23, 1988

Related U.S. Application Data

[63] Continuation of Ser. No. 291, Feb. 13, 1987, abandoned, which is a continuation of Ser. No. 904,149, Sep. 5, 1986, abandoned.

[51] Int. Cl.$^4$ .......................... C07K 7/06; C07K 5/06; C07K 5/08; C07K 5/10; C07D 277/04; C07D 263/02; C07D 207/00; C07D 207/12; C07D 211/36

[52] U.S. Cl. .................................. 530/329; 530/330; 530/331; 548/533; 548/215; 548/536; 548/200; 548/537; 548/550; 546/243

[58] Field of Search ........................ 530/329, 330, 331; 548/533, 215, 536, 200, 537, 580; 546/243

[56] References Cited

U.S. PATENT DOCUMENTS 4,680,284 7/1987 Luly et al. ........................... 530/331

Primary Examiner—Delbert R. Phillips
Attorney, Agent, or Firm—Lawrence T. Welch

[57] ABSTRACT

The present invention provides novel renin-inhibiting peptides of the formula X-$A_6$-$B_7$-$C_8$-$D_9$-$E_{10}$-$F_{11}$-$G_{12}$-$H_{13}$- $I_{14}$-Z, wherein the $E_{10}$–$F_{11}$ moiety is a dihydroxyethylene isostere, X and Z are terminal groups, and the remaining variables are absent or are amino acid residues. Such inhibitors are useful for the control of hypertension.

3 Claims, No Drawings

NOVEL RENIN INHIBITING PEPTIDES HAVING A DIHYDROXYETHYLENE ISOSTERE TRANSITION STATE INSERT

CROSS REFERENCE TO RELATED APPLICATIONS

This application is a continuation of co-pending PCT application PCT/US87/00291, filed 13 February 1987, which is a continuation of application Ser. No. 904,149, filed 05 September 1986, both are now abandoned.

DESCRIPTION

BACKGROUND OF THE INVENTION

The present invention provides novel compounds. More particularly, the present invention provides novel renin-inhibiting peptide analogs. Most particularly, the present invention provides renin-inhibitory compounds having a dihydroxyethylene isostere transition state insert. The renin inhibitors provided herein are useful for the diagnosis and control of renin-dependent hypertension.

Renin is an endopeptidase which specifically cleaves a particular peptide bond of its substrate (angiotensinogen), of which the N-terminal sequence in equine substrate is for example:

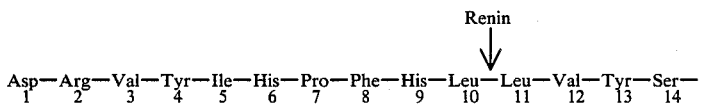

IA as found by L. T. Skeggs et al, J. Exper. Med. 106, 439 (1957). Human renin substrate has a different sequence as recently discovered by D. A. Tewkesbury et al, Biochem. Biophys. Res. Comm. 99, 1311 (1981). It may be represented as follows:

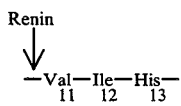

IB and having the sequence to the left of the arrow (↓) being as designated in formula IA above.

Renin cleaves angiotensinogen to produce angiotensin I, which is converted to the potent pressor angiotensin II. A number of angiotensin I converting enzyme inhibitors are known to be useful in the treatment of hypertension. Inhibitors of renin are also useful in the treatment of hypertension.

INFORMATION DISCLOSURE

A number of renin-inhibitory peptides have been disclosed. Thus, U.S. Pat. No. 4,424,207, and European published application Nos. 45,665 and 104,041 disclose certain peptides with the dipeptide at the 10,11-position containing an isotere bond. A number of statine derivatives stated to be renin inhibitors have been disclosed, see, e.g., European published application Nos. 77,028; 81,783; and 114,993; and U.S. Pat. Nos. 4,478,826; 4,470,971 and 4,479,941. Terminal disulfide cycles have also been disclosed in renin inhibiting peptides; see, e.g., U.S. Pat. Nos. 4,477,440 and 4,477,441. Aromatic and aliphatic amino acid residues at the 10,11 position of the renin substrate are disclosed in U.S. Pat. No. 4,478,827. C-terminal amide cycles are disclosed in U.S. Pat. No. 4,485,099. Certain tetrapeptides are disclosed in European publications 111,266 and 77,027. Further, European published application No. 118,223 discloses certain renin inhibiting peptide analogs where the 10-11 peptide link is replaced by a one to four atom carbon or carbon-nitrogen link. Additionally, Holladay et al., in "Synthesis of Hydroxyethylene and Ketomethylene Dipeptide Isosteres", Tetrahedron Letters, Vol. 24, No. 41, pp. 4401–4404, 1983 disclose various intermediates in a process to prepare stereo-directed "ketomethylene" and "hydroxyethylene" dipeptide isosteric functional groups disclosed in the above noted U.S. Pat. No. 4,424,207. Evans, et al., J. Org. Chem., 50, 4615 (1985) discloses the synthesis of Hydroxyethylene Dipeptide Isosteres. See also, published European patent application 163,237, which discloses certain renin inhibiting peptides.

Additionally, published European Applications 45,161 and 53,017 disclose amide derivatives useful as inhibitors of angiotensin converting enzymes.

SUMMARY OF THE INVENTION

The present invention particularly provides a renin inhibitory peptide of the formula $X-A_6-B_7-C_8-D_9-E_{10}-F_{11}-G_{12}-H_{13}-I_{14}-Z$, wherein X is
(a) hydrogen,
(b) $C_1-C_5$alkyl
(c) $R_5-O-CH_2-C(O)-$,
(d) $R_5-CH_2-O-C(O)-$,
(e) $R_5-O-C(O)-$,
(f) $R_5-(CH_2)_n-C(O)-$,
(g) $R_4N(R_4)-(CH_2)_n-C(O)$,
(h) $R_5-SO_2-(CH_2)_q-C(O)-$,
(i) $R_5-SO_2-(CH_2)_q-O-C(O)-$, or
(j) $R_6-(CH_2)_i-C(O)-$;

wherein $A_6$ is absent or a divalent moiety of the formula $XL_1$, $XL_2$, or $XL_{2a}$ (refer to claim 1 below for formulas);

wherein $B_7$ is absent or a divalent moiety of the formula $XL_b$ wherein $C_8$ is absent or a divalent moiety of the formula $XL_1$, $XL_2$, or $XL_{2a}$;

wherein $D_9$ is a divalent moiety of the formula $XL_3$ or $XL_{2a}$, or wherein $C_8-D_9$ is $XL_7$ or $XL_{7a}$, or wherein $C_8-D_9$ are a monovalent moiety of the formula $XL_{7b}$ when X, $A_6$, and $B_7$ are absent;

wherein $E_{10}-F_{11}$ is a divalent moiety of the formula $XL_6$ or $XL_{6a}$;

wherein * indicates an asymmetric center which is either in the R os S configuration;

wherein $G_{12}$ is absent or a divalent moiety of the formula $XL_4$ or $XL_{4a}$;

wherein $H_{13}$ is absent or a divalent moiety of the formula $XL_4$;

wherein $I_{14}$ is absent or a divalent moiety of the formula $XL_5$;

wherein Z is
(a) $-O-R_{10}$,
(b) $-N(R_4)R_{14}$, or (c) $C_4$-$C_8$cyclic amino;
wherein R is
(a) isopropyl,
(b) isobutyl,
(c) phenylmethyl, or
(d) $C_3$-$C_7$cycloalkyl;
wherein $R_1$ is
(a) hydrogen,
(b) $C_1$-$C_5$alkyl,
(c) aryl,
(d) $C_3$-$C_7$cycloalkyl,
(e) —Het,
(f) $C_1$-$C_3$alkoxy, or
(g) $C_1$-$C_3$alkylthio;
wherein $R_2$ is
(a) hydrogen, or
(b) —CH($R_3$)$R_4$;
wherein $R_3$ is
(a) hydrogen,
(b) hydroxy,
(c) $C_1$-$C_5$alkyl,
(d) $C_3$-$C_7$cycloalkyl,
(e) aryl,
(f) —Het,
(g) $C_1$-$C_3$alkoxy, or
(h) $C_1$-$C_3$alkylthio;
wherein $R_4$ at each occurrence is the same or different and is
(a) hydrogen, or
(b) $C_1$-$C_5$alkyl;
wherein $R_5$ is
(a) $C_1$-$C_6$alkyl,
(b) $C_3$-$C_7$cycloalkyl,
(c) aryl,
(d) —Het, or
(e) 5-oxo-2-pyrrolidinyl;
wherein $R_6$ is
(a) hydrogen,
(b) C-$C_5$alkyl,
(c) —($CH_2$)$_p$—aryl,
(d) —($CH_2$)$_p$—Het,
(e) —($CH_2$)$_p$—$C_3$—$C_7$cycloalkyl,
(f) 1- or 2-adamantyl,
(g) —S—aryl,
(h) —S—$C_3$—$C_7$cycloalkyl, or
(i) —S—$C_1$—$C_6$alkyl;
wherein $R_7$ is
(a) hydrogen,
(b) $C_1$-$C_5$alkyl,
(c) hydroxy,
(d) amino $C_1$-alkyl-,
(e) guanidinyl $C_1$-$C_3$alkyl-,
(f) aryl,
(g) —Het,
(h) methylthio,
(i) —($CH_2$)$_p$—$C_3$—$C_7$cycloalkyl, or
(j) amino;
wherein $R_8$ is
(a) hydrogen,
(b) $C_1$-$C_5$alkyl,
(c) hydroxy,
(d) aryl,
(e) —Het,
(f) guanidinyl $C_1$-$C_3$alkyl-, or
(g) —($CH_2$)$_p$—$C_3$—$C_7$cycloalkyl;
wherein $R_9$ is
(a) hydrogen,
(b) hydroxy,
(c) amino $C_1$-$C_4$alkyl-, or
(d) guanidinyl $C_1$-$C_3$alkyl-;
wherein $R_{10}$ is
(a) hydrogen,
(b) $C_1$-$C_5$alkyl,
(c) —($CH_2$)$_n$$R_{16}$,
(d) —($CH_2$)$_n$$R_{17}$,
(e) $C_3$-$C_7$cycloalkyl,
(f) a pharmaceutically acceptable cation,
(g) —CH($R_{25}$)—$CH_2$—$R_{15}$, or
(h) —$CH_2$—CH($R_{12}$)—$R_{15}$;
wherein $R_{11}$ is —R or —$R_2$;
wherein $R_{12}$ is —($CH_2$)$_n$—$R_{13}$;
wherein $R_{13}$ is
(a) aryl,
(b) amino,
(c) mono-, di or tri-$C_1$-$C_3$alkylamino,
(d) —Het,
(e) $C_1$-$C_5$alkyl
(f) $C_3$-$C_7$cycloalkyl,
(g) $C_{12}$-$C_5$alkenyl,
(h) $C_3$-$C_7$cycloalkenyl,
(i) hydroxy,
(j) $C_1$-$C_3$alkoxy,
(k) $C_1$-$C_3$alkanoyloxy,
(l) mercapto,
(m) $C_1$-$C_3$alkylthio,
(n) —COOH,
(o) —CO—O—$C_1$—$C_6$alkyl,
(p) —CO—O—$CH_2$—($C_1$—$C_3$alkyl)—N($C_1$—$C_3$alkyl)$_2$,
(q) —CO—N$R_{22}R_{26}$;
(r) $C_4$-$C_7$cyclic amino,
(s) $C_4$-$C_7$cycloalkylamino,
(t) guanidyl,
(u) cyano,
(v) N-cyanoguanidyl,
(w) cyanoamino,
(x) (hydroxy $C_2$-$C_4$alkyl)amino, or
(y) di-(hydroxy$C_2$-$C_4$alkyl)amino;
wherein $R_{14}$ is
(a) hydrogen,
(b) $C_1$-$C_{10}$alkyl,
(c) —($CH_2$)$_n$—$R_{18}$,
(d) —($CH_2$)$_n$—$R_{19}$,
(e) —CH($R_{25}$)—$CH_2$—$R_{15}$,
(f) —$CH_2$—CH($R_{12}$)—$R_{15}$,
(g) (hydroxy $C_1$-$C_8$alkyl), or
(h) ($C_1$-$C_3$alkoxy)$C_1$-$C_8$alkyl;
wherein $R_{15}$ is
(a) hydroxy,
(b) $C_3$-$C_7$cycloalkyl,
(c) aryl,
(d) amino,
(e) mono-, di-, or tri-$C_1$-$C_3$alkylamino,
(f) mono- or di-[hydroxy $C_2$-$C_4$alkyl]amino,
(g) —Het,
(h) $C_1$-$C_3$alkoxy—,
(i) $C_1$-$C_3$alkanoyloxy-,
(j) mercapto,
(k) $C_1$-$C_3$alkylthio-,
(l) $C_1$-$C_5$alkyl,
(m) $C_4$-$C_7$cyclic amino,
(n) $C_4$-$C_7$cycloalkylamino,
(o) $C_1$-$C_5$alkenyloxy,
(p) $C_3$-$C_7$cycloalkenyl;
wherein $R_{16}$ is
(a) aryl, (b) amino,
(c) mono- or di-$C_1$-$C_3$alkylamino,
(d) hydroxy,
(e) $C_3$-$C_7$cycloalkyl,
(f) $C_4$-$C_7$cyclic amino, or
(g) $C_1$-$C_3$alkanoyloxy;
wherein $R_{17}$ is
  (a) —Het,
  (b) $C_1$-$C_5$alkenyl,
  (c) $C_3$-$C_7$cycloalkenyl,
  (d) $C_1$-$C_3$alkoxy,
  (e) mercapto,
  (f) $C_1$-$C_3$alkylthio,
  (g) —COOH,
  (h) —CO—O—$C_1$—$C_6$alkyl,
  (i) —CO—O—$CH_2$—($C_1$—$C_3$alkyl)—N($C_1$—$C_3$alkyl)$_2$,
  (j) —CO—$NR_{22}R_{26}$,
  (k) tri-$C_1$-$C_3$alkylamino,
  (l) guanidyl,
  (m) cyano,
  (n) N-cyanoguanidyl,
  (o) (hydroxy $C_2$-$C_4$alkyl)amino,
  (p) di-(hydroxy $C_2$-$C_4$alkyl)amino, or
  (q) cyanoamino;
wherein $R_{18}$ is
  (a) amino,
  (b) mono-, or di-$C_1$-$C_3$alkylamino,
  (c) $C_4$-$C_7$cyclic amino; or
  (d) $C_4$-$C_7$cycloalkylamino;
wherein $R_{19}$ is
  (a) aryl,
  (b) —Het,
  (c) tri-$C_1$-$C_3$alkylamino,
  (d) $C_3$-$C_7$cycloalkyl,
  (e) $C_1$-$C_5$alkenyl,
  (f) $C_3$-$C_7$cycloalkenyl,
  (g) hydroxy,
  (h) $C_1$-$C_3$alkoxy,
  (i) $C_1$-$C_3$alkanoyloxy,
  (j) mercapto,
  (k) $C_1$-$C_3$alkylthio,
  (l) —COOH,
  (m) —CO—O—$C_1$—$C_6$alkyl,
  (n) —CO—O—$CH_2$—($C_1$—$C_3$alkyl)—N($C_1$—$C_3$alkyl)$_2$,
  (o) —CO—$NR_{22}R_{26}$,
  (p) guanidyl,
  (q) cyano,
  (r) N-cyanoguanidyl,
  (s) cyanoamino,
  (t) (hydroxy $C_2$-$C_4$alkyl)amino,
  (u) di-(hydroxy $C_2$-$C_4$alkyl)amino; or
  (v) —$SO_3H$;
wherein $R_{20}$ is
  (a) hydrogen,
  (b) $C_1$-$C_5$alkyl, or
  (c) aryl-$C_1$-alkyl;
wherein $R_{22}$ is
  (a) hydrogen, or
  (b) $C_1$-$C_3$alkyl;
wherein $R_{23}$ is
  (a) —$(CH_2)_n$—OH,
  (b) —$(CH_2)_n$—$NH_2$,
  (c) aryl, or
  (d) $C_1$-$C_3$alkyl;
wherein $R_{25}$ is
  (a) hydrogen,
  (b) $C_1$-$C_3$alkyl, or
  (c) phenyl-$C_1$-$C_3$alkyl;
wherein $R_{26}$ is
  (a) hydrogen,
  (b) $C_1$-$C_3$-alkyl, or
  (c) phenyl-$C_1$-$C_3$alkyl;
wherein m is one or two;
wherein for each occurrence n is independently an integer of zero to five, inclusive;
wherein p is zero to 2 inclusive;
wherein q is 1 to 5, inclusive;
wherein Q is
  (a) —$CH_2$—,
  (b) —CH(OH)—,
  (c) —O—, or
  (d) —S—; and
wherein M is
  (a) —CO—, or
  (b) —$CH_2$—;
wherein aryl is phenyl or naphthyl substituted by zero to 3 to the following:
  (a) $C_1$-$C_3$alkyl,
  (b) hydroxy,
  (c) $C_1$-$C_3$alkoxy,
  (d) halo,
  (e) amino,
  (f) mono- or di-$C_1$-$C_3$alkyamino,
  (g) —CHO,
  (h) —COOH,
  (i) $COOR_{26}$,
  (j) $CONHR_{26}$,
  (k) nitro,
  (l) mercapto,
  (m) $C_1$-$C_3$alkylthio,
  (n) $C_1$-$C_3$alkylsulfinyl,
  (o) $C_1$-$C_3$alkylsulfonyl,
  (p) —N($R_4$)—$C_1C_3$alkylsulfonyl,
  (q) $SO_3H$,
  (r) $SO_2NH_2$,
  (s) —CN, or
  (t) —$CH_2NH_2$;
wherein —Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:
  (i) $C_1$-$C_6$alkyl,
  (ii) hydroxy,
  (iii) trifluoromethyl,
  (iv) $C_1$-$C_4$alkoxy,
  (v) halo,
  (vi) aryl,
  (vii) aryl $C_1$-$C_4$alkyl-,
  (viii) amino,
  (ix) mono- or di-$C_1C_4$alkylamino, and
  (x) $C_1$-$C_5$alkanoyl;
with the overall provisos that
  (1) $R_{18}$ or $R_{19}$ is hydroxy, mercapto, or amino, or a mono-substituted nitrogen containing group bonded through the nitrogen only when n is not one;
  (2) $R_{12}$ is —$(CH_2)_n$—$R_{13}$ and n is zero and both $R_{13}$ and $R_{15}$ are oxygen-, nitrogen-, or sulfur-containing substituents bonded through the hetero atom, only when the hetero atom is not also bonded to hydrogen;
  (3) $R_{17}$ or $R_{19}$ is —COOH only when n for that moiety is other than zero;

(4) $R_{16}$ or $R_{17}$ is an amino-containing substutient, hydroxy, mercapto, or —Het bonded through the hetero atom only when n for that substuent is an integer from two to five, inclusive;

(5) when $R_{12}$ is —$(CH_2)_n$—$R_{13}$ and n is zero, then $R_{13}$ and $R_{15}$ cannot both be —COOH; and (6) $R_{17}$ or $R_{19}$ is —Het, only when —Het is other than cyclic amino;

or a carboxy-, amino-, or other reactive group-protected form thereof;

or a pharmaceutically acceptable acid addition salt thereof.

These compounds are shown in relation to the human renin substrate as follows:

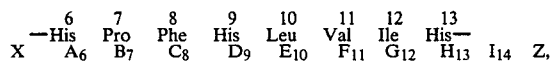

The present invention provides peptide inhibitors of renin which contain modification of positions $E_{10}$ and $F_{11}$, the site of action by renin. The renin inhibitors of this invention can be considered as analogs of the transition state of the hydrolysis by renin at the 10,11-position of its human substrate angiotensinogen. These modifications involve the insertion of diol-containing moieties at this position. These changes result in dramatic changes in potency over the normal leu-val at the 10,11-position.

Examples of pharmaceutically acceptable acid addition salts include: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophasphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_4)$alkyl refers to alkyl of one to 4 carbon atoms, inclusive, or methyl, ethyl, propyl, butyl, and isomeric forms thereof. $C_4-C_7$cyclic amino indicates a monocyclic group containing one nitrogen and 4 to 7 carbon atoms.

Examples of $(C_3-C_{10})$cycloalkyl which include alkyl-substituted cycloalkyl containing a total of up to 10 carbon atoms, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl, cyclononyl, cyclodecyl and isomeric forms thereof.

Examples of aryl include phenyl, naphthyl, (o-, m-, p-)tolyl, (o-, m-, p-)ethylphenyl, 2ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4- 2,3,6-, or 2,4,5-)trimethylphenyl, (o-, m-, or p-)fluorophenyl, (o-, m-, or p-trifluoromethyl)phenyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-)trifluoro-methylphenyl, (o-, m-, or p-)ethoxyphenyl, (4- or 5-)chloro-2-methoxy-phenyl, and 2,4-dichloro-(5-or 6-)methylphenyl, and the like.

Examples of —Het include: 2-, 3-, or 4-pyridyl, imidazolyl, indolyl, $N^{in}$-formyl-indolyl, $N^{in}$-$C_1$-$C_5$alkyl-C(O)-indolyl, [1,2,4]-triazolyl, 2-, 4-, or 5-pyrimidinyl, 2- or 3-thienyl, piperidinyl, pyrryl, pyrrolinyl, pyrrolidinyl, pyrazolyl, pyrazolinyl, pyrazolidinyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, thenyl, and benzothienyl. Each of these moieties may be substituted as noted above.

As would be generally recognized by those skilled in the art of organic chemistry, heterocycle as defined herein for —Het would not be bonded through oxygen or sulfur or through nitrogen which is within a ring and part of a double bond.

Halo is halogen (fluoro, chloro, bromo, or iodo) or trifluoromethyl.

Examples of pharmaceutically acceptable cations include: pharmaceutically acceptable metal cations, ammonium, amine cations, or quanternary ammonium cations. Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are also within the scope of this invention. Pharmacologically acceptable amine cations are those derived from primary, secondary, or tertiary amines.

The novel peptides herein contain both natural and synthetic amino acid residues. These residues are depicted using standard amino acid abbreviations (see, e.g., *Eur. J. Biochem.*, 138, 9 (1984)) unless otherwise indicated.

The renin inhibitors of this invention are useful for treating any medical condition for which it is beneficial to reduce the levels of active circulating renin. Examples of such conditions include renin-dependent hypertension, hypertension, hypertension under treatment with another antihypertension and/or a diuretic agent, congestive heart failure, angina, and post-myocardial infarction. The renin-angiotension system may play a role in maintenance of intracellular homeostasis: see Clinical and Experimental Hypertension, 86, 1739–1742 (1984) at page 1740 under Discussion.

The compounds of the present invention are preferably orally administered to humans to effect renin inhibition for the purpose of favorably affecting blood pressure. For this purpose, the compounds are administered from 0.1 mg to 1000 mg per kg per dose, administered from 1 to 4 daily. Other routes of administration, such as parenteral (including intravenous, intramuscular, and intraperioneal) are also employed. Equivalent dosages for such other routes of administration are thus employed.

The exact dose depends on the age, weight, and condition of the patient and on the frequency and route of administration. Such variations are within the skill of the practitioner or can readily be determined.

The compounds of the present invention may be in the form of pharmaceutically acceptable salts both those which can be produced from the free bases by methods well known in the art and those with which acids have pharmacologically acceptable conjugate bases.

Conventional forms and means for administering renin-inhibiting compounds may be employed and are described, e.g., in U.S. Pat. No. 4,424,207 which is incorporated by reference herein. Likewise, the amounts disclosed in the U.S. Pat. No. 4,424,207 are examples applicable to the compounds of the present invention.

The compounds of the present invention are preferably orally administered in the form of pharmocologically acceptable acid addition salts. Preferred pharmacologically acceptable salts for oral administration include the citrate and aspartate salts, although any pharmacologically acceptable salt is useful in this invention, including those listed above. These salts may be in hydrated or solvated form.

The renin-inhibiting compounds of this invention may be administered in combination with other agents used in antihypertensive therapy such as diuretics, $\alpha$ and/or $\beta$-adrenergic blocking agents, CNS-acting agents, adrenergic neuron blocking agents, vasodilators, angiotensin-converting enzyme inhibitors, and the like as described for example in published European patent application No. 156 318.

The compounds of the present invention are prepared as depicted in the charts and as described more fully in the Preparations and Examples.

There are described herein two possible syntheses of the aldehyde component (designated 9 in scheme 1). In scheme 1, the cisallylic alcohol 2 is prepared from the alkyne 1 following a known procedure, namely, by reaction of 1 with n-butyllithium and then reaction with paraformaldehyde; followed then by reduction with hydrogen gas in the presence of $Pd/BaSO_4$ (palladium on barium sulfate) in the presence of quinoline in a suitable solvent such as methanol to give 2. Asymmetric epoxidation (see J. Am. Chem. Soc. 102:5974 (2980) then affords the chiral epoxide 3. This is oxidized to the acid and then derivatized to the amide 4. Treatment of the epoxide 4 with magnesium azide gives the desired regioisomer 5, and the azide is reduced and protected as in the derivative 6. Conversion to the oxazolidine 7 is followed by a reductive unmasking of the amide to give the desired aldehyde 8.

In a shorter and therefore preferred, synthetic route (scheme2) addition of a vinyl Grignard to Boc-L-leucinal 9 gives a mixture of epimeric alcohols 10.

Since the direct addition of vinylmagnesium bromide to tertbutyloxycarbonyl-L-leucinal led to partial racemization, it is more desirable to use trityl-protected-L-leucinal. L-leucinol is tritylated and the hydroxyl group is then oxidized (Omura, et al, Tetrahedron 1978, 34, p. 1651) to the corresponding aldehyde. Addition of vinylmagnesium bromide afforded the mixture of epimeric alcohols. The trityl group is removed under acidic hydrolysis and the resulting amine is protected as the tertbutylocycarbonyl group to give 10. The corresponding oxazolidine mixture 11 is treated with ozone to give a mixture of aldehyde 8 and its epimer 8a. This mixture is equilibrated under alkaline condition to give a minimum of 10:1 mixture favoring the trans-isomer 8.

In scheme 3, the aldehyde 8 is added to the boron enolate of the chiral oxazolidinone 12 to the procedure of Evans (J. Am. Chem. Soc. 103:3099 (1981)). The predominate adduct 13 is derivatized to the crystalline trimethylsilyl ether. A single crystal x-ray structural determination confirms the predicted stereochemistry as that shown in compound 13. Reduction of the boronate of 13 removes the chiral auxiliary and gives the diol 14. This is derivatized to the differentially protected diol 15. Selective removal of the acetate followed by ruthenium oxidation gives the desired acid 16. In a slightly different variation, the oxazolidine 14 is equilibrated to the acetonide 17 which is then oxidized (see J. Org. Chem. 46:3936 (1981)), to the desired acid 18. Both the acids 16 and 18 are useful in the preparation of renin inhibitory peptides that contain Leu-Val diol the pseudo-dipeptide.

A representative peptide 23 is prepared as shown in scheme 4. The acid 16 is coupled to the known amine 19 to give compound 20. Exhaustive removal of protecting groups gives the amino-diol which is coupled to Boc—His(Ts)—OH to give compound 21. Treatment with trifluoroacetic acid to give the amine is followed by coupling with Boc—Phe—OH to afford compound 22. Removal of the tosyl group leads to the desired peptide 23.

Generally, the renin inhibiting polypeptides may be prepared by either polymer assisted or solution phase peptide synthetic procedures analogous to those described hereinafter or to those methods known in the art. For example, the carboxylic moiety of $N^{\alpha}$-t-butyloxycarbonyl (Boc)-substituted amino acid derivatives having suitable side chain protecting groups, if necessary, may be condensed with the amino functionality of a suitably protected amino acid, peptide or polymer-bound peptide using a conventional coupling protocol such as dicyclohexylcarbodiimide (DCC) and 1-hydroxybenzotriazole (HOBT) or diethylphosphoryl cyanide (DEPC) and triethylamine ($Et_3N$) in methylene chloride or dimethylformamide. The synthetic procedures used to incorporate the novel moieties herein are analgous to those described, for example, in U.S. Pat. Nos. 4,424,207; 4,470,971; 4,477,440; 4,477,441; 4,478,826; 4,478,827; 4,479,941; and 4,485,099, and copending application Ser. No. 753,198, filed 9 July 1985, and copending application Ser. No. 825,250, filed 3 February 1986, all of which are expressly incorporated by reference herein. See, also, published European patent application Nos. 45,161; 45,665; 53,017; 77,028; 77,029; 81,783; 104,041; 111,266; 114,993; and 118,223.

Following coupling reaction completion, the $N^{\alpha}$-Boc moiety may be selectively removed with 45% trifluoroacetic acid with or without 2% anisole (v/v) in methylene chloride. Neutralization of the resultant trifluoroacetate salt may be accomplished with 10% diisopropylethylamine or sodium bicarbonate in methylene chloride. In the case of polymer-assisted peptide synthesis, this stepwise, coupling strategy may be partially or completely automated to provide the desired peptide-polymer intermediates. Anhydrous hydrofluoric acid treatment of the peptide-polymer intermediate may then be used to effect simultaneous protecting group removal and cleavage of the peptide from its polymeric support. A notable exception to this includes $N^{in}$-formyl-indolyl-substituted peptides in which the $N^{in}$-formyl-indolyl moiety is stable to TFA or HF but may be removed by $NH_3$ or NaOH. Because FTrp is somewhat unstable to base in synthetic procedures, possibly causing lower yields, it may be desirable in solution phase synthesis to introduce the FTrp-containing moiety late in the synthetic sequence so that it is not exposed to such conditions.

The incorporation of $N^{in}$-formyl-Trp into compounds of the present invention is easily accomplished because of the commercial availability of $N^{\alpha}$-Boc-$N^{in}$- formyl-Trp-OH. However, the N$^{in}$-formyl moiety may be introduced into indolyl-substituted amino acid derivatives or related compounds by reaction with HCl-formic acid as reported in the literature, see A. Previero et al, Biochem. Biophys.-Acta 147, 453 (1967); Y. C. S. Yang et al, Int. J. Peptide Protein Res. 15, 130 (1980).

Generally, methods of alkylation useful in alkylating histidine for use in the present invention are found in Cheung, S. T. et al, Can. J. Chem., Vol 55, pp. 906–910 (1977). However it is now found that in Cheung, S. T. et al, methods it is critical that the reaction conditions for the alkylation of histidine be anydrous. Further, it is now found also that during work-up instead of adding water directly to the reaction mixture, it is preferred that a buffered aqueous solution be added to the reaction mixture, for example, aqueous sodium or potassium hydrogen sulfate.

Variations in the above description for starting materials, reactants, reaction conditions and required protecting groups to obtain other such N-alkylated compounds are known to an ordinarily skilled chemist or are readily available in the literature.

These peptides may also be prepared by the standard solid phase techniques of Merrifield. Appropriate protecting groups, reagents, and solvents for both the solution and solid phase methods can be found in "The Peptides: Analysis, Synthesis, and Biology," Vols. 1–5, eds. E. Gross and T. Meienhofer, Academic Press, NY, 1979–1983.

The compounds of the present invention may be in either free form or in protected form at one or more of the remaining (not previously protected) peptide, carboxyl, amino, hydroxy, or other reactive groups. The protecting groups may be any of those known in the polypeptide art. Examples of nitrogen and oxygen protection groups are set forth in T. W. Greene, Protecting Groups in Organic Synthesis, Wiley, New York, (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (Boc), benzyloxycarbonyl, acetyl, allyl, phthalyl, benzyl, benzoyl, trityl and the like.

DESCRIPTION OF THE PREFERRED EMBODIMENTS

The following Preparations and Examples illustrate the present invention.

In the Preparations and Examples below and throughout this document:
Ac is acetyl;
AMP is 2-(aminomethyl)pyridinyl;
BOC is t-butoxycarbonyl;
BOM is benzyloxymethyl;
Bz is benzyl;
C is centigrade
Celite is a filter aid;
CVDA is "Cha-Val diol" where Cha is 3-cycloxylalanyl, i.e. the moiety of the formula XL$_6$ wherein R$_1$ is cyclohexyl and R$_{11}$ is isopropyl and the configuration at each carbon atom with a * is (R);
DCC is dicyclohexylcarbodiimide;
DMF is dimethylformamide;
EtOAc is ethyl acetate;
g. is grams;
GEA is 2-(quanidylethyl)amino;
GMPMA is (3-(guanidylmethyl)phenyl)methylamino;
HPLC is high performance liquid chromatography;
IR is infra red spectra;
A Lindlar catalyst is a modified 5% palladium on calcium carbonate catalyst, obtained from Engelhard Industries and used for reduction;
LVDA is "Leu-Val diol," i.e., the moiety of the formula XL$_6$ wherein R$_1$ and R$_{11}$ are isopropyl and the configuration at each carbon atom with a * is (R);
M or mol is mole;
MBA is 2-methylbutylamino (racemic or optically active);
MBAS is 2S-methylbutylamino;
Me is methyl;
min. is minute;
ml is milliliter;
MS is mass spectroscopy;
NMHis is N$\alpha$-methyl-L-histidine;
NMR is nuclear magnetic resonance;
MOA1 is (1-naphthyloxy)acetyl;
p-TSA salt is para-toluene sulfonic acid salt;
Ph is phenyl;
POA is phenoxyacetyl;
RIP means a compound having the formula H-Pro-His-Phe-His-Phe-Phe-Val-Tyr-Lys-OH.2(CH$_3$C(O)OH).XH$_2$O which is a known renin-inhibiting peptide. Skellysolve B is as defined in the Merck Index, 10th edition;
TBDMS is t-butyldimethylsilyl;
TFA is trifluoroacetic acid;
THF is tetrahydrofuran;
TLC is thin layer chromatography;
Tos is p-toluenesulfonyl;
Tr is trityl (triphenylmethyl); and
2HPA is (±)-(2-hydroxypropyl)amino.

The wedge-shape line indicates a bond which extends above the plane of the paper relative to the place of the compound thereon.

The dotted line indicates a bond which extends below the plant of the paper relative to the place of the compound thereon.

Preparation 1

1-Hydroxy-5-methyl-2-hexyne

Refer to scheme 1.

To a solution of 77.7 ml of 1.57 M n-butyl lithium in hexane under argon, cooled to −78° C. is added dropwise over 20 min, a solution of 10.0 g (122 mmol) of 4-methyl-1-pentyne in 90 ml of dry ether. The reaction mixture is then allowed to warm to room temperature and 40 ml of dry tetrahydrofuran is added. The reaction mixture is recooled to 0° C. and 4.39 g (146 mmol) of paraformaldehyde is added. After stirring for 5 min, the reaction mixture is warmed to room temperature. After 1 h, the reaction mixture is heated to reflux for 2 h and 50 min, then cooled. The reaction mixture is poured over 100 ml of ice and swirled vigorously in an ice bath until everything is in solution. The reaction mixture is partitioned between either and water. The aqueous phase is extracted with 3×100 ml ether. Combined organics were extracted with 100 ml saturated aqueous NaCl, dried (MgSO$_4$), filtered and concentrated. Evaporated distillation (~20 torr; 150° C.) affords 13.38 g (119 mm, 98%) of desired titled alcohol.

$^1$H-NMR (CDCl$_3$): δ 0.97, 1.45, 1.57, 2.09, and 4.25.

Preparation 2

(Z)-1-Hydroxy-5-methyl-2-hexene

Refer to scheme 1.

A solution of 6.00 g (53.3 mmol) of 1-hydroxy-5-methyl-2-hexyne (Preparation 1) in 88.7 ml of methanol is treated with 3.2 ml of quinoline and 600 mg of Lindlar's catalyst (Pd/BaSO$_4$). The mixture is hydrogenated under an initial pressure of 52 psi. After 30 min, hydrogenation is stopped. The reaction mixture is filtered through Celite and concentrated. The residue is diluted with 200 ml of ether and washed with 2×50 ml of cold 1N aqueous HCl (saturated with NaCl), 50 ml saturated aqueous NaCl, 50 ml saturated aqueous NaHCO$_3$ and 50 ml saturated aqueous NaCl, dried (MgSO$_4$), filtered and concentrated. Evaporated distillation (~20 torr; 165° C.) affords 5.31 g (46.5 mmol, 87%) of the desired titled (Z)-alkene.

$^1$H-NMR (CDCl$_3$): δ 0.89, 1.26, 1.62, 1.97, 4.15, and 5.61, $^{13}$C-NMR CDCl$_3$): δ 22.29, 28.61, 36.56, 58.45, 129.47, and 131.29.

Preparation 3

2R,3R-Epoxy-5-methylhexanol

Refer to scheme 1 (2 to 3).

To 220 ml of dry dichloromethane, cooled to −20° C., under argon, is sequentially added 6.23 g (21.92 mmol) of titanium (IV) isoproxide and 5.50 g (26.31 mmol) of L-(+)-diethyltartrate. The resulting mixture is stirred for 5 min, then 2.50 g (21.92 mmol) of alcohol of Preparation 2 is added, followed by 9.76 ml (44.93 mmol) of 4.6 M t-butyl-hydroperoxide in toluene. The resulting reaction mixture is stored in a freezer (ca. −25° C.) overnight. The reaction mixture is cooled to −20° C., and then treated with 6.43 ml (87.88 mmol) of dimethyl sulfide. After stirring for 40 min, the cold reaction mixture is slowly cannulated into a vigorously stirred saturated (~5%) aqueous NaF solution (twice the volume of the original reaction mixture). Stirring is continued at room temperature for 48 h. The aqueous phase is saturated with solid NaCl and the gel-like precipitates are removed via filtration through Celite. The aqueous phase is extracted with 3×150 ml of dichloromethane and the combined organic phases are dried (MgSO4), filtered and then concentrated. The residue is diluted with 6.5 ml of ether and cooled to 0° C. and then treated with 5.3 ml of 1N aqueous sodium hydroxide. The biphasic mixture is stirred at 0° C. for exactly 30 min. The phases are separated and the aqueous phase is extracted with 2×25 ml of ether. The ethereal phase is extracted with 25 ml of saturated aqueous NaCl. The organic phase is dried (MgSO$_4$), filtered and then concentrated. Flash chromatography of the residue on silica gel with 30% ethyl acetate in hexane affords 2.40 g (18.4 mmol, 84%) of the titled epoxy alcohol.

$^1$H-NMR (CDCl$_3$): δ 0.96, 0.99, 1.48, 3.1, and 3.75. $^{13}$C-NMR (CDCl$_3$): δ 26.28, 26.56, 30.59, 40.48, 60.01, 60.66, 64.74; IR (neat 3408 cm$^{-1}$; [α]$_D$=3° (c=0.81, CHCl$_3$);

HRMS: (M−−CH$_3$)=115.0754 (calcd for C$_6$H$_{11}$O$_2$=115.0759).

Preparation 4

2R,3R-Epoxy-5-methylhexanoic acid

Refer to scheme 1.

To a solution of 669.5 mg (5.14 mmol) of the epoxy alcohol 3 in 10 ml carbon tetrachloride, 10 ml acetonitrole and 15 ml of water are added 4.50 g (21.07 mmol) of sodium meta periodate and 29.61 mg (0.113 mmol) of ruthenium trichloride trihydrate. The entire biphasic mixture is stirred vigorously at room temperature for 2 h. The reaction mixture is diluted with dichloromethane and phases are separated. The aqueous phase is extracted with 4×25 ml dichloromethane. Combined organics are dried (MgSO4), filtered and concentrated. The residue is diluted with 100 ml ether, and filtered through Celite. Filtrate is concentrated under reduced pressure to afford 701.9 mg (4.87 mmol, 95%) of the desired titled epoxy acid.

$^1$H-NMR (CDCl$_3$): δ 0.96, 1.0, 1.25, 1.51, 3.24, 3.54, and 9.42. $^{13}$C-NMR (CDCl$_3$): δ 26.09, 26.48, 30.22, 39.64, 56.19, 61.03, and 177.29.

IR (neat): 3418, 1734 cm$^{-1}$; [α]$_D$+8° (c=0.119, CHCl$_3$).

HRMS: m/z=144.0786 (calcd. for 144.0786).

Preparation 5

2R,3R-Epoxy-5-methyl-N-methyl-N-methoxy-hexanamide

Refer to scheme 1. Preparations 4 and 5 herein illustrate 3 to 4 in scheme 1.

To a stirred solution of 414.2 mg (2.87 mmol) of the epoxy acid (Preparation 4) in 10 ml of dry dichloromethane is added 420.8 mg (4.31 mmol) of O,N-dimethyl-hydroxyamine hydrochloride and 464.6 mg (4.50 mmol) of triethylamine followed by dropwise addition of 703.0 mg (4.31 mmol) of diethylphosphoryl cyanide. After stirring for 3 h at room temperature, the reaction is partitioned between dichloromethane and saturated aqueous NaHCO$_3$. The aqueous phase is extracted with 3×20 ml of dichloromethane. The combined organic phases are dried (MgSO$_4$), filtered and concentrated. Flash chromatography of the residue on silica gel with 30% ethyl acetate in hexane affords 495.2 mg (2.64 mmol, 92%) of the desired epoxy amide.

$^1$H-NMR (CDCl$_3$): δ 0.95, 0.98, 1.5, 3.28, 3.32, 3.74 and 3.82. $^{13}$C-NMR (CDCl$_3$): δ 26.09, 26.55, 30.25, 36.48, 39.97, 56.66, 60.16, and 65.46.

IR (neat 1680 cm$^{-1}$. [α]$_D$=+86° (c=0.51, CHCl$_3$).

1HRMS: m/z 187.1209 (calcd for 187.1208).

Preparation 6

3S-Azido-2R-hydroxy-5-methyl-N-methoxy-N-methylhexanamide

Refer to scheme 1 (4 to 5).

To a stirred solution of 1.213 g (8.42 mmol) of the epoxy amide (Preparation 5) in 5.5 ml of dry methanol is added 2.27 g (21.05 mmol) of freshly prepared magnesium azide. The reaction mixture is heated under reflux for 2.5 h, then cooled and concentrated. The residue is partitioned between dichloromethane and saturated aqueous NaHCO$_3$. The aqueous phase is extracred with 3×30 ml of dichloromethane. The combined organic phases are dried (MgSO$_4$), filtered and concentrated. The resulting yellowish solid is recrystallized from hexane to afford 1.24 g (5.39 mmol, 64%) of desired titled azide. MP 60°–61° C.

$^1$H-NMR 0.98, 1.63, 3.28, 3.65, 3.71 and 4.38. $^1$H-NMR (CDCl$_3$): δ $^{13}$C-NMR (CDCl$_3$): δ 26.21, 26.35, 28.89, 36.56, 42.81, 64.20, 65.21, 75.19, and 175.93.

IR (mull) 3286, 2115, 1650 cm$^{-1}$. [α]$_D$=+130° (c=0.77, CHCl#3).

FAB HRMS: [M+H]$^+$ at m/z=231.1444 (calcd for 231.1457).

Preparation 7

3S-Amino-2R-hydroxy-5-methyl-N-methoxy-N-methylhexanamide

Refer to scheme 1.

To a solution of 1.71 g (7.42 mmol) of the azide of Preparation 6 in 18.0 ml of dry methanol is added 358 mg of 10% palladium on carbon. The reaction mixture is hydrogenated under an initial pressure of 50 psi. After 1 h, the hydrogenation is stopped. The reaction mixture is filtered through Celite and concentrated to afford 1.51 g (742 mmol, 100%) of desired titled free amine.

$^1$H-NMR (CDCl$_3$): δ 0.94, 1.38, 1.85, 3.26, 3.72, and 4.33.

IR (CHCl$_3$) 3450 and 1660 cm$^{-1}$.

Preparation 8

2R-Hydroxy-3S-(tert-butyloxycarbonylamino)-5-methyl-N-methyl-N-methoxy hexanamide Refer to scheme 1. Preparations 7 and 8 herein illustrate 5 to 6 in scheme 1.

To a stirred solution of 1.50 g (7.42 mmol) of the free amine of Preparation 7 in 14 ml of dry tetrahydrofuran, cooled to 0° C., is added 1.69 g (7.86 mmol) of di-t-butyl dicarbonate. After stirring at room temperature for 3 h, the reaction mixture is concentrated. Flash chromatography of the residue on silica gel with 30% ethyl acetate in hexane affords 1.44 g (4.73 mmol, 64%) of the desired titled compound.

$^1$H-NMR (CDCl$_3$): δ 0.94, 1.39, 3.22, and 3.76. $^{13}$C-NMR (CDCl$_3$): δ 26.24, 28.51, 32.08, 36.81, 45.25, 53.50, 65.01, 74.30, 82.75, 159.26, and 177.04.

IR (mull): 3510, 3305, 1679 cm$^{-1}$. [α]$_D$ = +9° (c=0.57, CHCl$_3$). MS=231.

Anal. Calcd. for C$_{14}$H$_{28}$N$_2$O$_5$:
C, 55.29; H, 9.20; N, 9.20.
Found C, 55.16; H, 9.45; N, 8.70.

Preparation 9

2,2-Dimethyl-3-(tert-butyloxycarbonyl)-4S-(2-methylpropyl)-N-methyl-N-methoxy-5R-oxazolidinecarboxamide Refer to scheme 1 (6 to 7).

To a stirred solution of 1.44 g (4.74 mmol) of the alcohol of Preparation 8 in 29 ml of dry N,N-dimethylformamide is added 3.42 g (47.4 mmol) of 2-methoxypropene and 45.1 mg (0.237 mmol) of p-toluenesulfonic acid monohydrate. After stirring at room temperature for 1 h, the solution is heated at 40° C. for 2.5 h. The reaction mixture is cooled and then neutralized with solid sodium bicarbonate. After stirring for 1 h, the reaction mixture is filtered and concentrated. The N,N-dimethylformamide is removed via evaporative distillation. Flash chromatography of the residue on silica gel with 30% ethyl acetate in hexane affords 1.46 g (4.24 mmol, 90%) of the desired titled compound.

$^1$H-NMR (CDCl$_3$): δ 0.94, 1.48, 1.58, 3.23 and 3.76. $^{13}$C-NMR (CDCl$_3$): δ 25.15, 27.56, 29.24, 32.11, 36.33, 46.91, 60.63, 65.04, 80.90, 83.22, 99.06, and 154.99.

FAB HRMS [M+H]$^+$ at m/z 345.2404 (calcd for 345.2389).

Preparation 10

2,2-Dimethyl-3-(tert-butyloxycarbonyl)-4S-(2-methylpropyl)-5R-oxazolininecarboxaldehyde Refer to scheme 1 (7 to 8).

To a stirred solution of 2.0 g (5.81 mmol) of the amide of Preparation 9 in 25 ml of dry ether, cooled to 0° C., is added dropwise 29 ml (29.06 mmol) of a 1.0 M solution of lithium aluminum hydride in ether. After stirring for 10 min, the reaction mixture is treated with ethyl acetate, then with 1.0 ml of water and 4.0 ml of a 1.0 M aqueous MaOH. After 5 min, anhydrous magnesium sulfate is added and reaction mixture is warmed to room temperature, filtered and concentrated. Evaporative distillation (0.25 torr, 180° C.) affors 1.17 g (4.10 mmol, 71%) of desired titled aldehyde which is used immediately.

$^1$H-NMR (CDCl$_3$): δ 0.96, 1.46, 1.57, 1.61, 4.12, and 9.82.

MS=270.

Preparation 11

Nα-tert-Butyloxycarbonyl-L-leucinal

To a stirred solution of 3.80 g (29.95 mmol) of distilled oxalyl chloride in 80 ml of dry dichloromethane, cooled to −78° C. is added dropwise 4.50 g (57.60 mmol) of dry dimethylsulfoxide. After 10 min, 5.00 g (23.04 mmol) of Boc-L-leucinal in 36 ml of dry dichloromathane is added dropwise via addition funnel. After 15 min, the reaction mixture is treated with 16.6 ml (119.80 mmol) of dry triethylamine. After 5 min, the reaction mixture is warmed to room temperature. The reaction mixture is poured into 300 ml of pentane and water is added to dissolve the salts, then the reaction mixture is partitioned between saturated aqueous NaHCO$_3$ and pentane. The aqueous phase is extracted with pentane (4x). The organic phases are combined, dried (MgSO$_4$), filtered and concentrated to afford 4.95 g (23.04 mmol, 100%) of desired aldehyde, which was used immediately in the next reaction.

$^1$H-NMR (CDCl$_3$): δ 0.96, 1.45 and 9.59.

Preparation 12

4S-(tert-Butyloxycarbonyl)amino-6-methyl-1-heptene-3R-ol

Refer to scheme 2 (9 to 10).

To 46.1 ml (46.10 mmol) of 1.0 M vinyl magnesium bromide in tetrahydrofuran, cooled to −30° C., under argon is carefully added dropwise via addition funnel 4.95 g (23.04 mmol) of freshly prepared Boc-L-leucinal (Preparation 11) in 46 ml of dry tetrahydrofuran (addition is completed over 25 min). After 5 min, the reaction mixture is poured into an ice cooled stirred solution of saturated aqueous NH$_4$Cl. After 5 min, the reaction mixture is allowed to warm to room temperature, then diluted with ether and washed with saturated aqueous NH$_4$Cl, caturated aqueous NaHCO$_3$ and saturated aqueous NaCl. The organic phase is dried (MgSO$_4$), filtered and concentrated. Purification of the residue by medium resure liquid chromatography on silica gel (Lobar C) using 5–10% ethyl acetate in hexane affords 542.6 mg (2.52 mmol) of unreacted starting aldehyde, 595.1 mg of starting aldehyde and desired titled alkene, and 3.72 g (15.30 mmol, 67%) of desired titled alkene.

$^1$H-NMR (CDCl$_3$): δ 0.92, 1.43, 5.25, and 5.78.

IR (neat): 3361, 1690 cm$^{-1}$.

FAB HRMS: [M+H]$^+$ at m/z=244.1910 (calcd for 244.1913).

Preparation 13

2,2-Dimethyl-3-(tert-butyloxycarbonyl)-4S-(2-methylpropyl)-5R,S-ethenyl oxazolidine Refer to scheme 2 (10 to 11).

To a stirred solution of 3.72 g (15.28 mmol) of the alcohol of Preparation 12 in 30 ml of dry dichloromethane is added 11.02 g (152.88 mmol) of 2-methoxypropene and 192.0 mg (0.764 mmol) of pyridinium-p-toluenesulfonate. After stirring at room temperature for 4 h, the reaction mixture is neutralized with solid sodium bicarbonate. After 1 h, the reaction mixture is filtered and concentrated. Flash chromatography of the residue on silica gel with 7% ethyl acetate in hexane affords 4.32 g (15.28 mmol, 100%) of desired titled alkene.

$^1$H-NMR (CDCl$_3$): δ 0.94, 1.48, 1.51, 1.54, 1.56, 1.60, 5.25, and 5.75.

IR (neat): 1700 cm$^{-1}$. MS (M—CH$_3$)=268.

Preparation 14

2,2-Dimethyl-3-(tert-butyloxycarbonyl)-4S-(2-methylpropyl)-5R,S-oxazolidine aldehyde Refer to scheme 2 (11 to 8 and 8a).

A stirred solution of 5.04 g (17.81 mmol) of alkene of Preparation 13 in 75 ml of dry dichloromethane and 7.5 of dry methanol, cooled to −78° C., is ozonized until the solution turned blue (~40 min). The excess ozone was removed in a stream of nitrogen. The reaction mixture is treated with 3.09 g (23.93 mmol) of trimethylphosphite. After stirring for 10 min, the reaction mixture is warmed to room temperature. The reaction mixture is partitioned between dichloromathane and saturated aqueous NaHCO$_3$. The aqueous phase is extracted with dichloromethane. The combined organic phases are dried (MgSO$_4$), filtered and concentrated. Flash chromatography of the residue on silica gel with 20% ethyl acetate in hexane affords 3.56 g (12.49 mmol, 70%) of desired titled aldehydes as 1.7:1 mixture of isomers 8 and 8a.

$^1$H-NMR (CDCl$_3$): δ 0.96, 1.46, 1.48, 1.56, 1.61, 1.66, 4.24, 9.72, and 9.82.

Preparation 15

2,2-Dimethyl-3-(tert-butyloxycarbonyl)-4R-(2-methylpropyl)-5R,S-oxazolidinecarboxaldehyde Refer to scheme 2 (11 to 8 and 8a).

To a stirred solution of 3.3 g (11.57 mmol) of the aldehydes 8 and 8a in 46.2 ml of dry methanol is added 4.8 g (34.73 mmol) of anhydrous potassium carbonate. The reaction mixture is heated in a 40° C. oil bath for 14 h. The reaction mixture is cooled to room temperature and filtered through Celite and concentrated. The residue is diluted with dichloromethane and washed with water, saturated aqueous NaHCO$_3$ and saturated aqueous NaCl. The organic phase is dried (MgSO$_4$), filtered and concentrated. Evaporative distillation (0.25 torr, 180° C.) of the residue affords 221 g (7.75 mmol, 67%) of desired titled aldehyde (>15:1; 8:8a).

$^1$H-NMR (CDCl$_3$): δ 0.96, 1.46, 1.57, 1.61, 4.13, and 9.92.

Preparation 16

3-(1-Oxo-3-methylbutyl)-4R-methyl-5S-phenyl-2-oxazolidinone

To a stirred solution of 6.04 g (34.08 mmol) of 4R-methyl-5S-phenyl-2-oxazolidinone in 76 ml of dry tetrahydrofuran, cooled to −78° C., is slowly added, via addition funnel, 22.8 ml (35.09 mmol) of 1.57 M n-butyllithium in hexane. After stirring for 5 min, 4.93 g (40.89 mmol) of isovaleryl chloride is added dropwise. The reaction mixture is warmed to room temperature. After 30 min, the reaction mixture is treated with 15 ml of saturated aqueous NaHCO$_3$, and concentrated. The residue is partitioned between either and 1N aqueous NaOH. The aqueous layer is extracted with 75 ml ether. The combined organic phases are washed with 30 water, 30 ml saturated aqueous NaCl, dried (MgSO$_4$), filtered and concentrated. Evaporated distillation (0.3 torr, 200° C.) of the yellow residue affords 8.45 g (32.33 mmol, 95%) of a thick oil which solidifies upon standing, mp 52°-53° C.

$^1$H-NMR (CDCl$_3$): δ 0.88, 0.97, 2.12, 2.75, 2.81, 4.77, 5.59, and 7.45.

$^{13}$C-NMR (CDCl$_3$): δ 18.46, 26.33, 29.05, 47.91, 58.63, 82.78, 129.57, 132.60, 137.36, and 176.33.

IR (mull): 1770 cm$^{-1}$. [α]$_D$= +50° (c=0.95, CHCl$_3$).
HRMS=261.1371 (calcd. for 261.1365). C$_{15}$H$_{19}$NO$_3$
Calcd: C, 69.02; H, 7.27; N, 5.36.
Found: C, 68.92; H, 7.43; N, 5.35.

Preparation 17

3-N-(tert-butyloxycarbonyl)-4S-isobutyl-2,2-dimethyl-5R-[3-[(4R-methyl-2-oxo-5S-phenyl-oxazolidin-3-yl)-3-oxo-2R-isopropyl-1R-hydroxy]propyl]oxazolidine Refer to scheme 3 (8 and 12 to 13).

To a stirred solution of 1.07 g (4.11 mmol) of the acyloxazolidinone of Preparation 16 in 4.1 ml of dry dichloromethane, cooled to 0° C., is added 1.24 g (4.52 mmol) of dibutylboron triflate followed by 640.7 mg (4.92 mmol) of diisopropylethylamine. After 30 min, the reaction mixture is recooled to −78° C. and then 1.17 g (4.11 mmol) of freshly distilled aldehyde (compound 8 of Preparation 15) is added in 2.8 ml of dichloromethane with 1.0 ml rinse. After 30 min, the reaction mixture is warmed to room temperature. After 90 min the reaction mixture is recooled to 0° C. and then 3.4 ml of pH 7 phosphate buffer is rapidly added followed by 6.8 ml of methanol and 3.4 ml of 30% aqueous H$_2$O$_2$ in 6.8 of methanol. After 1 h, the reaction mixture is partitioned between dichloromethane and pH 7 phosphate buffer/water. The aqueous phase is then extracted with 3×70 ml of dichloromethane. The combined organic phases are dried (MgSO$_4$), filtered and concentrated. Flash chromatography of the residue on silica gel with 20% ethyl acetate in hexane affords 1.48 g (2.71 mmol, 66%) of the desired aldol titled product.

$^1$H-NMR (CDCl$_3$): δ 1.00, 1.47, 1.56, 1.63, 4.0, 4.8, 5.6, and 7.35.

IR (mull): 3493, 1702, 1693 cm$^{-1}$. [α]$_D$= +13° (c=0.94, CHCl$_3$).

FAB HRMS: [M+H]$^+$ at m/z 547.3396 (calcd for 547.3383).

Preparation 18

3-N-(tert-butyloxycarbonyl-4S-isobutyl-2,2-dimethyl-5R-[3-[(4R-methyl-2-oxo-5S-phenyl-oxazolidin-3-yl)-3-oxo-2R-isopropyl-1R-(trimethylsilyloxy)]propyl]oxazolidinone To a stirred solution of 200 mg (0.36 mmol) of the oxazolidinone (Preparation 17), cooled to −20° C., is added 156.02 mg (1.45 mmol) of 2,6-lutidene followed by 162.05 mg (0.73 mmol) of freshly distilled trimethylsilyl triflate. After 15 min, the reaction mixture is quenched with saturated aqueous NaHCO$_3$ and then warmed to room temperature. The reaction mixture is partitioned between dichloromethane and saturated aqueous NaHCO$_3$. The aqueous phase is extracted with 3×10 ml of dichloromethane. The combined organic phases are dried (MgSO$_4$), filtered and concentrated. The residue is chromatographed on 14 g of silica gel with 5 to 15% ethyl acetate in hexane to afford 215.9 mg (0.349 mmol, 96%) of the desired titled trimethylsilyl ether.

$^1$H-NMR (CDCl$_3$): δ (relative to TMS ether) 0.0, 0.84, 1.27, 1.15, 3.72, 4.16, 4.62, 5.44, and 7.17.

FAB HRMS: [M+H]$^+$ at m/z 619.3803 (calcd. for 619.3778).

Preparation 19

2R-Isopropyl-3-(4S-isobutyl-2,2-dimethyl-3-N-tert-butyloxycarbonyl-oxazolidin-5R-yl)-1,3-propanediol Refer to scheme 3 (13 to 14).

To a stirred solution of 329.2 mg (0.60 mmol) of the oxazolidinone of Preparation 17 in 2.5 ml of dry tetrahydrofuran is treated successively with 54.22 mg (0.90 mmol) of glacial acetic acid and 120.7 mg (0.66 mmol) of tributylboron. After 90 min at room temperature, the reaction mixture is cooled to 0° C. and 26.2 mg (1.20 mmol) of lithiumborohydride in 0.92 ml of dry tetrahydrofuran is added dropwise over 30 sec. After 90 min, the reaction mixture is warmed to room temperature for 30 min, then recooled to 0° C. and treated with 2.0 ml of methanol, 2.0 ml of pH 7 phosphate buffer and 1.0 ml of 30% aqueous hydrogen peroxide. The mixture is partitioned between dichloromethane and pH 7 phosphate buffer. The aqueous phase is extracted with 4×10 ml of dichloromethane. The combined organic phases are dried (MgSO$_4$), filtered and concentrated. Flash chromatography of the residue on silica gel with 20% ethyl acetate in hexane affords 216.3 mg (0.58 mmol, 96%) of the desired titled diol as a thick oil which crystallized upon standing, and 26 mg (0.04 mmol) of unreacted starting material.

$^1$H-NMR (CDCl$_3$): δ 0.99, 1.47, 1.51, 1.65, 2.57, 3.78, and 4.05.

FAB HRMS: [M+H]$^+$ at m/z 374.2893 (calcd for 374.2906.

Preparation 20

1-O-Acetyl-2R-isopropyl-3-(4S-isobutyl-2,2-dimethyl-3-N-tert-butyloxycarbonyl-oxazolidin-5R-yl)-1,3R-propanediol To a stirred solution of 210.9 mg (0.56 mmol) of the diol of Preparation 19, in 2.2 ml of dry dichloromethane is added 68.6 mg (0.67 mmol) of dry triethylamine followed by 68.5 mg (0.62 mmol) of acetylimidazole and a catalytic amount of 4-dimethylaminopyridine. The reaction mixture is heated in a 40° C. oil bath for 24 h, then cooled to room temperature and treated with 68.6 mg (0.67 mmol) of dry triethylamine and 68.5 mg (0.62 mmol) of acetylimidazole. The reaction mixture is again heated in a 40° C. oil bath for 8 h. The reaction mixture is cooled to room temperature, diluted with dichloromethane and washed with saturated aqueous NaHCO$_3$. The aqueous phases are dried (MgSO$_4$), filtered and concentrated. Flash chromatography of the residue on silica gel with 15% ethyl acetate in hexane affords 228.4 mg (0.55 mmol, 97%) of the desired titled acetate.

$^1$H-NMR (CDCl$_3$): δ 1.00, 1.47, 1.63, 2.03, and 4.00.

FAB HRMS: [M+H]$^+$ at m/z 416.2982 (calcd for 416.3012).

Preparation 21

1-O-Acetyl-3R-O-tert-butyldimethylsilyl-2R-Isopropyl-3-(4S-isobutyl-2,2-dimethyl-3-N-tert-butyloxycarbonyl-oxazolidin-5R-yl)-1,3R-propanediol Refer to scheme 3.

To a stirred solution of 169.5 mg (0.41 mmol) of the acetate of Preparation 20 in 1.6 ml of dry dichloromethane, cooled to 0° C. is added dropwise 69.95 mg (0.65 mmol) of distilled 2,6-lutidene followed by 118.76 mg (0.45 mmol) of freshly distilled tert-butyldimethylsilyl triflate. After 15 min, the reaction mixture is treated with saturated aqueous NaHCO$_3$ and then warmed to room temperature. The reaction mixture is partitioned between dichloromethane and saturated aqueous NaHCO$_3$. The aqueous phase is extracted with 3×10 ml of dichloromethane. The combined organic phases are dried (MgSO$_4$), filtered and concentrated. Flash chromatography of the residue on silica gel with 5 to 20% ethyl acetate in hexane affords 50.8 mg (0.96 mmol, 25%), 20.8 mg (0.05 mmol) of starting acetate, 13.8 mg (0.03 mmol) of secondary acetate (due to acetate migration), and 80.2 mg (0.16 mmol) of primary silyl ether.

$^1$H-NMR (CDCl$_3$): δ (relative to TBS ether) 0.00, 0.02, 0.86, 1.33, and 1.87.

FAB HRMS: [M+H]$^+$ at m/z=530.3859 (calcd for 530.3877).

Preparation 22

3R-O-tert-Butyldimethylsilyl-2R-isopropyl-3-(4S-isobutyl-2,2-dimethyl-3-N-tert-butyloxycarbonyloxazolidin-5R-yl)-1,3R-propanediol Refer to scheme 3.

To a stirred solution of 50.8 mg (01.095 mmol) of the protected acetate of Preparation 21 in 0.19 ml of dry methanol is added 39.7 mg (0.287 mmol) of anhydrous potassium carbonate. After 14 h at room temperature, the reaction mixture is filtered through Celite and then concentrated. The residue is diluted with dichloromethane, washed with 5 ml of saturated aqueous NaHCO$_3$, dried (MgSO$_4$), filtered and concentrated. The residue is chromatographed 5.0 g of silica gel with 5% ethyl acetate in hexane to afford 41.4 mg (0.086 mmol, 89%) of desired titled alcohol.

$^1$H-NMR (CDCl$_3$): δ (relative to TBS ether) 0.0, 0.05, 0.84, 0.94, 1.39, 1.44, 1.65, and 4.0.

FAB HRMS: [M+H]$^+$ m/z 488.3753 (calcd for 488.3771).

Preparation 23

2R-Isopropyl-3R-tert-butyldimethylsilyloxy-3-(4S-isobutyl-2,2-dimethyl-3-N-tert-butyloxycarbonyl-5R-oxazolidinyl)propanoic acid Refer to scheme 3 (15 to 16).

To a stirred solution of 41.4 mg (0.085 mmol) of the alcohol of Preparation 22 in 0.16 ml of carbon tetrachloride, 0.16 ml of acetonitrile and 0.24 ml of water is added 77.5 mg (0.340 mmol) of periodic acid and 0.48 mg (0.002 mmol) of ruthenium trichloride trihydrate. The biphasic mixture is stirred vigorously at room temperature for 2 h. The reaction mixture is diluted with dichloromethane and the phases are separated. The aqueous phase is extracted with 5×10 ml of dichloromethane. The combined organic phases are dried (MgSO$_4$), filtered and concentrated. The residue is chromatographed on silica gel with 5% ethyl acetate in hexane to afford 26.7 mg (0.53 mmol, 63%) of the desired acid.

$^1$H-NMR (CDCl$_3$): δ (relative to TBS ether) 0.00, 0.01, 0.76, 0.91, 1.31, 1.40, 1.58, 2.5, and 4.0.

FAB HRMS: [M+H]$^+$ at m/z 502.3570 (calcd for 502.3564).

Preparation 24

2R-Isopropyl-[5R-(1S-tert-butyloxycarbonylamino-3-methylbutyl)-2,2-dimethyl-4R-dioxolane]ethanol Refer to scheme 3 (14 to 17).

A stirred solution of 21.9 mg (0.059 mmol) of the diol of Preparation 19 in 0.5 ml of a 0.1 M solution of pyridinium-p-toluenesulfonate in dichloromethane is heated in a 40° C. oil bath overnight. The reaction mixture is cooled, concentrated and chromatographed directly on 2.5 g of silica gel with 15 to 40% ethyl acetate in hexane to afford 14.7 mg (0.039 mmol, 67%) of the desired titled alcohol and 1.8 mg (0.005 mmol) of a triol.

$^1$H-NMR (CDCl$_3$): δ 1.00, 1.37, 1.44, and 3.82.

FAB HRMS: [M+H]$^+$ at m/z 374.2886 (calcd for 374.2906).

Preparation 25

2R-Isopropyl-[5R-(1S-tert-butyloxycarbonyl-amino-3-methylbutyl)-2,2-dimethyl-4R-dioxolane]ethanoic acid Refer to scheme 3 (17 to 18).

To a stirred solution of 16.1 mg (0.043 mmol) of the alcohol of Preparation 24 in 0.08 ml of carbon tetrachloride, 0.08 ml of acetonitrile and 0.12 ml of water is added 39.3 mg (0.172 mmol) of periodic acid and a catalytic amount of ruthenium trichloride trihydrate. The biphasic mixture is vigorously stirred at room temperature for 2 h. The reaction mixture is diluted with dichloromethane and the phases were separated. The aqueous phase is extracted with 4×10 ml of dichloromethane. The combined organic phases are dried (MgSO$_4$), filtered and concentrated. The residue is chromatographed on 2.3 g of silica gel with 50% ethyl acetate in hexane to afford 13.5 mg (0.034 mmol, 81%) of the desired titled acid.

¹H-NMR (CDCl₃): δ 1.00, 1.41, 1.44 and 6.50.

Preparation 26

4-Methyl-2-S-(triphenylmethyl)amino-1-pentanol

To a stirred solution of 3.0 g (25.6 mmole) of L-leucinol in 26 mL of anhydrous dichloromethane is added 2.84 g (28.1 mmol) of triethylamine followed by 7.13 g (25.6 mmol) of triphenylmethyl chloride. After 70 min at room temperature, the reaction mixture is poured into 200 mL of ethyl acetate and extracted with two 75 mL portions of half-saturated aqueous NaCl. The aqueous phase is extracted with two 100 mL portions of ethyl acetate. The combined organic phases are dried (MGSO₄), filtered and concentrated. Flash chromatography of the residue on silica gel using 15% ethyl acetate in hexane with 0.1% added pyridine affords 7.17 g (20.0 mmol, 85%) of the desired alcohol.

H-NMR (CDCl₃): δ 0.65 (m, 6H), 3.15 (m, 1H), 7.25 (m, 15H);

IR (neat) 3336, 2954, 1490 cm⁻¹; $[\alpha]_D$ +27° (C=0.27, CHCl₃);

FAB-HRMS; m/z 360.2327 (calc'd for $C_{25}H_{29}NO$, 360.2327);

Anal. ($C_{25}H_{29}NO$) C, H, N.

Preparation 27

4-Methyl-2S-(triphenylmethyl)amino-1-pentanal

To a stirred solution of 3.13 g (24.7 mmol) of distilled oxalyl chloride in 50 mL of dry dichloromethane, cooled to −78°, is added dropwise 3.70 g (47.4 mmol) of dry dimethylsulfoxide in 1.0 mL of dichloromethane. After 10 min, 6.81 g (19.0 mmol) of 4-methyl-2S-triphenylmethylamino-1-pentanol in 50 mL of dry dichloromethane is added dropwise via cannula. After 15 min, the reaction mixture is treated with 13.7 mL (98.6 mmol) of triethylamine. After 5 min, the reaction mixture is warmed to room temperature and then poured into 500 mL of pentane and 200 mL of water to dissolve the salts. The reaction mixture is then partitioned between saturated aqueous NAHCO₃ and pentane. The aqueous phase is extracted with five portions of pentane. The organic phases are combined, dried (MgSO₄), filtered and then concentrated to afford 6.76 g (19.0 mmol, 100%) of the desired aldehyde, which is immediately used in the next reaction.

Preparation 28

3R and 3S-Hydroxy-6-methyl-4S-(triphenylmethyl)amino-1-heptene

To 38 mL (38 mmol) of a 1.0 M solution of vinyl magnesium bormide in tetrahydrofuran, cooled to −30°, under argon with stirring, is carefully added dropwise via cannula 6.76 g (19.0 mmol) of the freshly prepared 4-methyl-2S-triphenylmethylamino-1-pentanal in 38 mL of dry tetrahydrofuran. After 5 min, the reaction mixture is poured into a stirred ice cold solution of saturated aqueous NH₄Cl. After 5 min, the reaction mixture is warmed to room temperature, then diluted with ether and washed successively with saturated aqueous NH₄Cl, saturated aqueous NaHCO₃ and saturated aqueous NaCl. The organic phase is dried (MgSO₄), filtered and then concentrated. The resulting yellow thick oil is passed through a pad of florisil using 20% ethyl acetate in hexane. Concentration of the filtrate affords 7.11 g (96%) of compound 2.

¹H-NMR (CDCl₃): δ 0.5 (d, 3H,J=4Hz), 0.7 (d, 3H,J=4Hz), 1.25 (m, 3H), 2.5 (m, 1H), 5.5 (m, 3H), 7.5 (m, 15H);

IR (neat) 3345, 2955, 1490 cm⁻¹;

FAB-HRMS: m/z 386.2503 (calc'd for $C_{27}H_{31}NO$, 386.2484).

Preparation 29

4S-tert-Butyloxycarbonylamino-3R- and 3S-hydroxy-6-methyl-1-heptene

To a stirred solution of 7.11 g (18.5 mmol) of the compound of Preparation 28 above in 185 mL of dry methanol is added 7.10 g of DOWEX 50W-X8 resin. After 14h at room temperature, 9.0 g (84.9 mmol) of solid sodium carbonate is added. After 40 min, at room temperature, the reaction is filtered through celite and the filtrate is concentrated. The resulting residue is triturated with dichloromethane, filtered and then concentrated. To this residue is added 75 mL of dry tetrahydrofuran and 4.22 g (19.6 mmol) of di-tert-butyl dicarbonate. After stirring for 14h at room temperature, the reaction mixture is concentrated. Flash chromatography of the resulting residue on silica gel using 20% ethyl acetate in hexane affords 4.13 g (17.0 mmol, 92%) of the title compound.

¹H-NMR (CDCl₃) δ 0.92 (2×s, 6H,J=7Hz), 1.43 (s, 9H). 5.25 (m, 2H), 5.78 (m,1H);

IR (neat) 3361, 1690 cm⁻¹;

FAB-HRMS: m/z 244.1989 (calc'd for $C_{13}H_{25}NO_3$, 244.1913).

Preparations 30–34

The CVDA insert is obtained by using the processes of Scheme 2 starting with N-trityl-3-cyclohexyl-L-alaninal (the Boc-3-cyclohexyl-L-alaninal is known: Boger, et al., *J. Med. Chem.*, 28, 1779 (1985)) to produce (Preparation 30) 2,2-dimethyl-3-(tert-butyloxycarbonyl)-4S-(cyclohexylmethyl)-5R-oxazolidine aldehyde (and 5S enantiomer) having physicochemical data as follows:

¹H-NMR (CDCl₃): δ 0.73–2.0, 1.48, 1.60, 1.66, 3.22, 9.82.

FAB HRMS: [M+H]⁺ at M/Z=326.2315 (Calc'd for 326.2331). $[\alpha]_D$ = +11° (C=1.01, CHCl₃).

IR (mull): 2926, 2853, 1728, 1701 cm⁻¹

This is used as the starting material for processes of Scheme 3 to prepare the following compounds having the physicochemical data as follows:

Preparation 31

3N-(tert-butyloxycarbonyl)-4S-cyclopropylmethyl-2,2-dimethyl-5R-[3-[(4R-methyl-2-oxo-5S-phenyloxazolindin-3-yl)-3-oxo-2R-isopropyl-1R-hydroxy]-propyl]oxazolidine ¹H-NMR (CDCl₃): δ 0.89–1.0, 1.5, 1.7, 4.0, 4.8, 5.6, 7.4.

IR (mull): 3470, 2868, 2853, 1789, 1692 cm⁻¹. $[\alpha]_D$ = +18° (C=1.00, CHCl₃).

FAB HRMS: [M+H]⁺ at M/Z=587.3706 (Calc'd for 587.3696).

Anal. Calc'd for $C_{33}H_{51}N_2O_7$: C, 67.47; H, 8.68; N, 4.76.

Found C, 67.34; H, 8.68; N, 4.87.

Preparation 32

2R-Isopropyl-3-(4S-cyclohexylmethyl-2,2-dimethyl-3-N-tert-butyloxycarbonyl-oxazolidin-5R-yl)-1,3R-propanediol ¹H-NMR (CDCl₃): δ 0.96, 1.47, 1.51, 1.65, 2.53, 3.76, 4.07.

IR (neat): 3470, 2926, 1700, 1680 cm⁻¹. $[\alpha]_D$ = +11° (C−0.32, CHCl₃).

FAB MS: [M=H]⁺ at M/Z=414.

Preparation 33

2R-Isopropyl-[5R-(1S-tert-butyloxycarbonylamino-3-methylbutyl)-2,2-dimethyl-4R-dioxolane]ethanol ¹H-NMR (CDCl₃): δ 1.0–2.0, 0.99, 1.36, 1.44, 2.90, 3.82, 4.75.

IR (mull): 3397, 3267, 2954, 1671 cm⁻¹. $[\alpha]_D = -26°$ (C=0.89, CHCl₃).

FAB HRMS: [M+H] at M/Z=414.3208 (Calc'd for 414.3219).

Anal. Calc'd for $C_{23}H_{43}NO_5$: C, 66.84; H, 10.40; N, 3.38.

Found C, 66.79; H, 10.29, N, 3.42.

Preparation 34

2R-Isopropyl-[5R-(1S-tert-butyloxycarbonyl-amino-2-(cyclohexylethyl)-2,2-dimethyl-4R-dioxoland]ethanoic acid ¹H-NMR (CDCl₃) δ 1.0–2.0, 1.05, 1.34, 1.44, 2.5, 4.02, 4.85, 9.25.

IR (mull): 3333, 3934, 1710, 1649 cm⁻¹.

FAB HRMS: [M+H]+ at M/Z 428.3007 (Calc'd for 428.3012). Anal. Calc'd for $C_{23}H_{41}NO_6$: C, 64,65; H, 9.95; N, 3.27.

Found: C, 64.23; H, 9.77; N, 3.16.

EXAMPLE 1

2R-Isopropyl-3R-tert-butyldimethylsilyloxy-3-(2,2-dimethyl-4S-isobutyl-3-N-tert-butyloxycarbonyl-5R-oxazolidinyl)propanoyl-L-isoleucyl-2-pyridylmethylamide Refer to scheme 4 (19 to 20).

To a stirred solution of 30 mg (60 μmol) of the acid of Preparation 23, 27 mg (0.122 mmol) of L-isoleucyl-2-pyridylmethylamide and 10 μl (72 μmol) of triethylamine in 0.5 ml of dichloromethane is added 10 μl (65 μmol) of diethylphosphoryl cyanide. After 14 h, the reaction mixture is directly chromatographed on silica gel with 1:1=ethyl acetate:hexane to give 34 mg (48 μmol, 80%) of compound 20 (the titled compound).

¹H-NMR (CDCl₃) δ 0.11, 0.16, 0.89, 1.45, 1.45 and 1.65.

EXAMPLE 2

[5S-[(N-tert-Butyloxycarbonyl-N$^{im}$-tosyl-L-histidyl-)amino-3R,4R-dihydroxy-2R-isopropyl-7-methyloctanoyl]-L-isoleucyl-2-pyridylmethylamide Refer to scheme 4 (20 to 21).

A solution of 34 mg (48 μmol) of the compound of Example 1 and 30 mg of p-toluenesulfonic acid monohydrate in 1 ml of methanol is heated at 60° C. for 30 min. To the cooled reaction mixture is added excess solid NaHCO₃ and the resulting mixture is then concentrated. The residue is triturated with several portions of dichloromathane and the filtrate concentrated. The resulting residue is chromatographed on silica gel with 10% methanol (saturated with gaseous ammonia) in dichloromethane to give 12 mg (26.6 μmol, 55%) of the free amine.

To a stirred solution of 12 mg (26.6 μmol) of this amine, 22 mg (53.7 μmol) of N-tert-butyloxycarbonyl-N$^{im}$-tosyl-L-histidine and 10 μl (72 μmol) of triethylamine in 0.5 ml of dichloromethane is added 10 μl (65 μmol) of diethylphosphoryl cyanide. After 1 day, the reaction mixture is directly chromatographed on silica gel with 5% methanol in ethyl acetate to give 20 mg (23.8 μmol, 89%) of the titled compound.

¹H-NMR (CDCl₃): δ 1.42 and 2.43.

EXAMPLE 3

[5S-[[(N-tert-Butyloxycarbonyl-L-phenylalanyl)-N$^{im}$-tosyl-L-histidyl]amino]-3R,4R-dihydroxy-2R-isopropyl-7-methyl-octanoyl]-L-isoleucyl-2-pyridylmethylamide Refer to scheme 4 (21 to 22).

A solution of 20 mg (23.8 μmol) of the compound of Example 2 in 0.5 ml of dichloromethane and 0.5 ml of trifluoroacetic acid is allowed to stand at room temperature (about 20°–25° C.) for 1 h. The concentrated reaction mixture is partitioned between dichloromethane and saturated aqueous NaHCO₃. The organic phase is dried (MgSO₄) and then concentrated to give the free amine.

To a stirred solution of this free amine, 15 mg (56 μmol) of N-tert-butyloxycarbonyl-L-phenylalanine and 10 μl (72 μmol) of triethyamine in 0.5 Ml of dichloromethane is added 10 μl (65 μl) of diethylphosphoryl cyanide. After 14 h, the concentrated reaction mixture is chromatographed on silica gel with 5% methanol in ethyl acetate to give 14 mg (14.2 μmol, 60%) of the titled compound.

EXAMPLE 4

[5S-[[(N-tert-Butyloxycarbonyl-L-phenylalanyl)-L-histidyl]amino]-3R,4R-dihydroxy-2R-isopropyl-7-methyloctanoyl]-L-isoleucyl-2pyridylmethylamide Refer to scheme 4 (22 to 23).

A solution of 14 mg (14.2 μmol) of the compound of Example 3 and 14 mg (0.10 mmol) of 1-hydroxy-benzotriazole in 0.5 of methanol is stirred at room temperature for 14 h. The concentrated reaction mixture is chromatographed on silica gel with 10% methanol (saturated with gaseous ammonia) in dichloromethane to give 9 mg (10.8 μmol, 76%) of the titled peptide.

FAB HRMS: [M+H]+ at m/z=835.5047 (calcd 835.5082).

Following the procedures of the preceding examples, compounds are prepared:
wherein $Z_1$-$A_6$-$B_7$-$C_8$-$D_9$ is
 POA-His;
 NOA1-His;
 Boc-Phe-His; or
 Boc-HPhe-His;
wherein $E_{10}$-$F_{11}$ is LVDA; and
wherein $G_{12}$-$H_{13}$-$I_{14}$-Z is
 Ile-AMP;
 Ile-GEA;
 Ile-GEA;
 Ile-GMPMA;
 —MBA; or
 —2HPA.

EXAMPLES 5–16

Following the procedures herein described, the additional compounds of Table A are prepared. Physicochemical data for the compounds of Table A are presented in Table B. The Chemical Abstracts names for these compounds are:

(EXAMPLE 5)

[5S-[(1′-Naphthoxyacetyl)-L-histidyl]amino-3R,4R-dihydroxy-2R-isopropyl-7-methyloctanoyl]-L-isoleucyl-2-pyridylmethylamide;

(EXAMPLE 6)

[5S-(Phenoxyacetyl-L-histidyl)amino-3R,4R-dihydroxy-2R-isopropyl-7-methyloctanoyl]-L-isoleucyl-2-pyridylmethylamide;

(EXAMPLE 7)

[5S-(Phenoxyacetyl-L-histidyl)amino-3R,4R-dihydroxy-2R-isopropyl-7-methyloctanoyl]-2S-methylbutylamide;

(EXAMPLE 8)

[5S-[(1'-Naphthoxyacetyl)-L-histidyl]amino-3R,4R-dihydroxy-2R-isopropyl-7-methyloctanoyl]-2S-methylbutylamide;

(EXAMPLE 9)

[5S-[[(N-tert-Butyloxycarbonyl-L-phenylalanyl)-L-histidyl]amino]-3R,4R-dihydroxy-2R-isopropyl-7-methyloctanoyl]-2S-methylbutylamide;

(EXAMPLE 10)

[5S-[[(N-tert-Butyloxycarbonyl-L-phenylalanyl)-(N$^\alpha$-methyl-L-histidyl)]amino-3R,4R-dihydroxy-2R-isopropyl-7-methyloctanoyl]-L-isoleucyl-2-pyridylmethylamide;

(EXAMPLE 11)

[5S-[[(N-tert-Butyloxycarbonyl-L-propyl)-L-phenylalanyl-(N$^\alpha$-methyl-L-histidyl)]amino]-3R,4R-dihydroxy-2R-isopropyl-7-methyloctanoyl]-L-isoleucyl-2-pyridylmethylamide;

(EXAMPLE 12)

[5S-[[(N-tert-butyloxycarbonyl-L-phenylalanyl)-L-histidyl]amino]-6-cyclohexyl-3R,4R-dihydroxy-2R-isopropylhexanoyl]-L-isoleucyl-2-pyridylmethylamide;

(EXAMPLE 13)

[5S-[[(N-tert-Butyloxycarbonyl-L-phenylalanyl)-(N$^\alpha$-methyl-L-histidyl)]amino]-6-cyclohexyl-3R,4R-dihydroxy-2R-isopropylhexanoyl]-L-isoleucyl-2-pyridylmethylamide;

(EXAMPLE 14)

[5S-[[(N-Acetyl-L-prolyl)-L-phenylalanyl-(N$^\alpha$-methyl-L-histidyl)]amino]-6-cyclohexyl-3R,4R-dihydroxy-2R-isopropylhexanoyl]-L-isoleucyl-2-pyridylmethylamide;

(EXAMPLE 15)

[5S-[(1'-Naphthoxyacetyl)-L-histidyl]amino-6-cyclohexyl-3R,4R-dihydroxy-2R-isopropylhexanoly]-L-isoleucyl-2-pyridylmethylamide; and

(EXAMPLE 16)

[5S-[[(N-Acetyl-L-prolyl)-L-phenylalanyl-(N$^\alpha$-methyl-L-histidyl)]amino]-3R,4R-dihydroxy-2R-isopropyl-7-methyloctanoyl]-L-isoleucyl-2-pyridylmethylamide

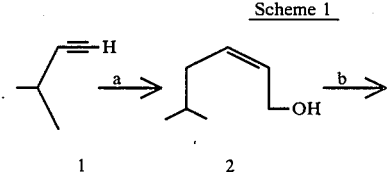

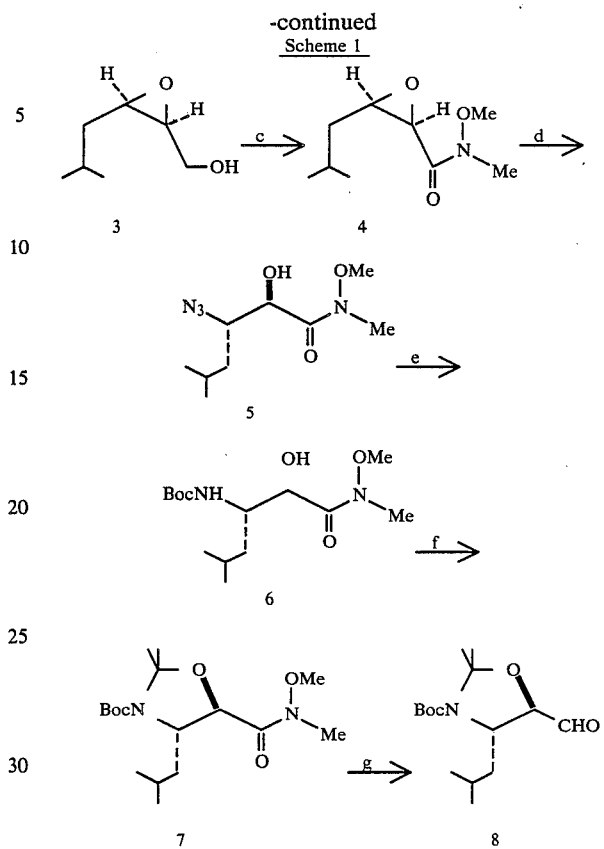

(a) n-BuLi, (HCHO)$_n$; Pd/BaSO$_4$, quinoline, H$_2$; (b) (CH$_3$)$_3$COOH, Ti(OPr$^i$)$_4$, L-(+)-diethyltartrate; (c) RuCl$_3$, NaIO$_4$; NHMeOMe, DEPC, Et$_3$H; (d) Mg(N$_3$)$_2$; (e) Pd/C, H$_2$; [(CH$_3$)$_3$—C—O—CO]$_2$O; (f) CH$_2$=C(OMe)Me, H$^+$; (g) LiAlH$_4$.

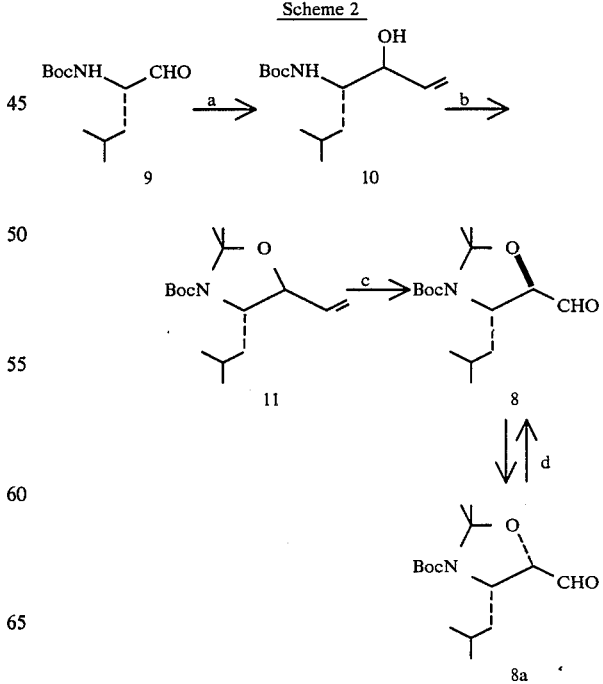

For the step 9→10, it is more desirable to use the trityl protecting group in place of the Boc group.

(a) CH$_2$=CHMgBr, THF; (b) CH$_2$=C(OCH$_3$)CH$_3$, pyr·TsOH, CH$_2$Cl$_2$; (c) O$_3$, CH$_3$OH/CH$_2$Cl$_2$; P(OCH$_3$)$_4$; (d) K$_2$CO$_3$, CH$_3$OH.

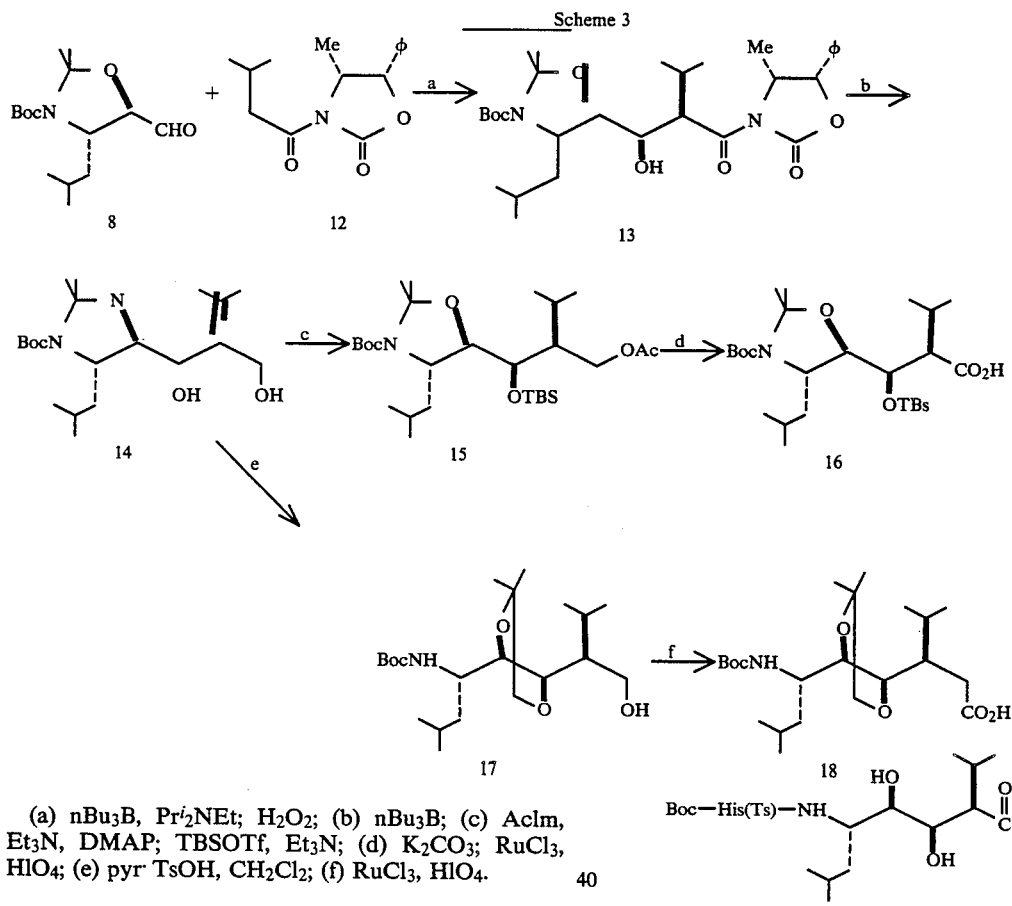

Scheme 3

(a) nBu$_3$B, Pr$^i_2$NEt; H$_2$O$_2$; (b) nBu$_3$B; (c) AcIm, Et$_3$N, DMAP; TBSOTf, Et$_3$N; (d) K$_2$CO$_3$; RuCl$_3$, HIO$_4$; (e) pyr·TsOH, CH$_2$Cl$_2$; (f) RuCl$_3$, HIO$_4$.

Scheme 4

(a) acid 16, DEPC, Et$_3$N; (b) CH$_3$OH, TsOH; Boc-His(Ts)—OH, DEPC, Et$_3$N; (c) TFA, CH$_2$Cl$_2$; Boc-Phe-OH, DEPC Et$_3$N; (d) HOBT, CH$_3$OH.

TABLE A

| Example | X | A$_6$ | B$_7$ | C$_8$ | D$_9$ | E$_{10}$/F$_{11}$ | G$_{12}$ | H$_{13}$ | I$_{14}$ | Z |
|---|---|---|---|---|---|---|---|---|---|---|
| 4 | Boc | abs | abs | Phe | His | LVDA | Ile | abs | abs | AMP |
| 5 | NOAl | abs | abs | abs | His | LVDA | Ile | abs | abs | AMP |
| 6 | POA | abs | abs | abs | His | LVDA | Ile | abs | abs | AMP |

TABLE A-continued

| Example | X | $A_6$ | $B_7$ | $C_8$ | $D_9$ | $E_{10}/F_{11}$ | $G_{12}$ | $H_{13}$ | $I_{14}$ | Z |
|---|---|---|---|---|---|---|---|---|---|---|
| 7 | POA | abs | abs | abs | His | LVDA | abs | abs | abs | MBAS |
| 8 | NOAl | abs | abs | abs | His | LVDA | abs | abs | abs | MBAS |
| 9 | Boc | abs | abs | Phe | His | LVDA | abs | abs | abs | MBAS |
| 10 | Boc | abs | abs | Phe | NMHis | LVDA | Ile | abs | abs | AMP |
| 11 | Boc | abs | Pro | Phe | NMHis | LVDA | Ile | abs | abs | AMP |
| 12 | Boc | abs | abs | Phe | His | CVDA | Ile | abs | abs | AMP |
| 13 | Boc | abs | abs | Phe | NMHis | CVDA | Ile | abs | abs | AMP |
| 14 | Ac | abs | Pro | Phe | NMHis | CVDA | Ile | abs | abs | AMP |
| 15 | NOAl | abs | abs | abs | His | CVDA | Ile | abs | abs | AMP |
| 16 | Ac | abs | Pro | Phe | NMHis | AVDA | Ile | abs | abs | AMP |

TABLE B

| | Physicochemical Data | |
|---|---|---|
| | HPLC Retention Data | |
| Example | Time (min.)[1] | Ms$[M + H]^+$ |
| 4 | 10.66 | 835.5047 |
| 5 | 11.02 | 772.4404 |
| 6 | 9.66 | 722.4276 |
| 7 | 9.12 | 588.3782 |
| 8 | 10.92 | 638.3944 |
| 9 | 10.57 | 701.4634 |
| 10 | 10.35 | 849.5214 |
| 11 | 12.03 | 946.5703 |
| 12 | 13.06 | 875.5365 |
| 13 | 12.94 | 889.5574 |
| 14 | 16.98 | 928.5639 |
| 15 | 13.66 | 812.4689 |
| 16 | 13.88 | 888.5353 |

[1]CONDITIONS: 90% $CH_3OH$ and 10% aqueous phosphate pH 3 buffer monitored at 254 nm, RP-18, 10 micron particle size, 1.5 mL/min.

What is claimed is:

1. A renin inhibitory peptide of the formula X-$A_6$-$B_7$-$C_8$-$D_9$-$E_{10}$-$F_{11}$-$G_{12}$-$H_{13}$-$I_{14}$-Z,
wherein X is
(a) hydrogen,
(b) $C_1$-$C_5$alkyl
(c) $R_5$—O—$CH_2$—C(O)—,
(d) $R_5$—$CH_2$—O—C(O)—,
(e) $R_5$—O—C(O)—,
(f) $R_5$—$(CH_2)_n$—C(O)—,
(g) $R_4N(R_4)$—$(CH_2)_n$—C(O),
(h) $R_5$—$SO_2$—$(CH_2)_q$—C(O)—,
(i) $R_5$—$SO_2$—$(CH_2)_q$—O—C(O)—, or
(j) $R_6$—$(CH_2)_i$—C(O)—;
wherein $A_6$ is absent or a divalent moiety of the formula $XL_1$, $XL_2$, or $XL_{2a}$

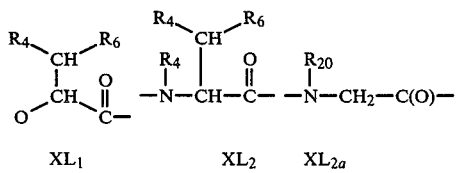

wherein $B_7$ is absent or a divalent moiety of the formula $XL_b$

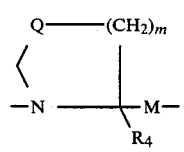

wherein $C_8$ is absent or a divalent moiety of the formula $XL_1$, $XL_2$, or $XL_{2a}$;

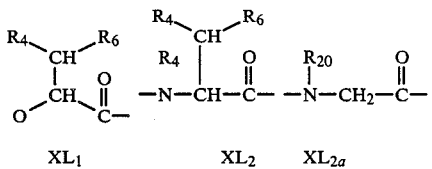

wherein $D_9$ is a divalent moiety of the formula $XL_3$ or $XL_{2a}$, or

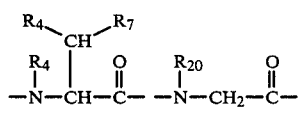

wherein $C_8$–$D_9$ is $XL_7$ or $XL_{7a}$, or

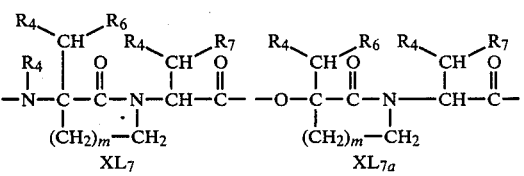

wherein $C_8$–$D_9$ are a monovalent moiety of the formula $XL_{7b}$ when X, $A_6$, and $B_7$ are absent;

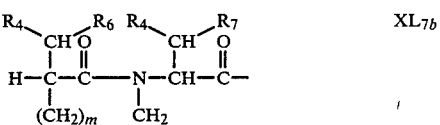

wherein $E_{10}$-$F_{11}$ is a divalent moiety of the formula $XL_6$ or $XL_{6a}$;

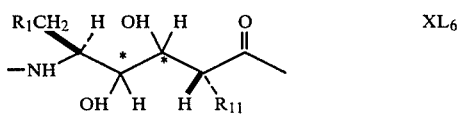

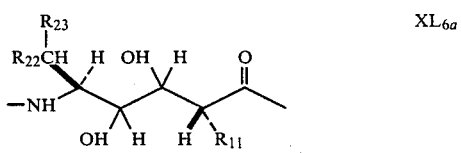

wherein * indicates an asymmetric center which is either in the R or S configuration;

wherein $G_{12}$ is absent or a divalent moiety of the formula $XL_4$ or $XL_{4a}$;

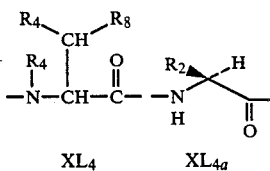

wherein $H_{13}$ is absent or a divalent moiety of the formula $XL_4$;

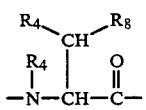

wherein $I_{14}$ is absent or a divalent moiety of the formula $XL_5$;

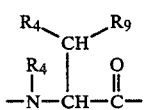

wherein Z is
(a) $-O-R_{10}$,
(b) $-N(R_4)R_{14}$, or
(c) $C_4-C_8$cyclic amino;
wherein R is
(a) isopropyl,
(b) isobutyl,
(c) phenylmethyl, or
(d) $C_3-C_7$cycloalkyl;
wherein $R_1$ is
(a) hydrogen,
(b) $C_1-C_5$alkyl,
(c) aryl,
(d) $C_3-C_7$cycloalkyl,
(e) —Het,
(f) $C_1-C_3$alkoxy, or
(g) $C_1-C_3$alkylthio;
wherein $R_2$ is
(a) hydrogen, or
(b) $-CH(R_3)R_4$;
wherein $R_3$ is
(a) hydrogen,
(b) hydroxy,
(c) $C_1-C_5$alkyl,
(d) $C_3-C_7$cycloalkyl,
(e) aryl,
(f) —Het,
(g) $C_1-C_3$alkoxy, or
(h) $C_1-C_3$alkylthio;
wherein $R_4$ at each occurrence is the same or different and is
(a) hydrogen, or
(b) $C_1-C_5$alkyl;
wherein $R_5$ is
(a) $C_1-C_6$alkyl,
(b) $C_3-C_7$cycloalkyl,
(c) aryl,
(d) —Het, or
(e) 5-oxo-2-pyrrolidinyl;
wherein $R_6$ is (a) hydrogen,
(b) $C-C_5$alkyl,
(c) $-(CH_2)_p$—aryl,
(d) $-(CH_2)_p$—Het,
(e) $-(CH_2)_p-C_3-C_7$cycloalkyl,
(f) 1- or 2-adamantyl,
(g) —S—aryl,
(h) $-S-C_3-C_7$cycloalkyl, or
(i) $-S-C_1-C_6$alkyl;
wherein $R_7$ is
(a) hydrogen,
(b) $C_1-C_5$alkyl,
(c) hydroxy,
(d) amino $C_1$-alkyl-,
(e) guanidinyl $C_1-C_3$alkyl-,
(f) aryl,
(g) —Het,
(h) methylthio,
(i) $-(CH_2)_p-C_3-C_7$cycloalkyl, or
(j) amino;
wherein $R_8$ is
(a) hydrogen,
(b) $C_1-C_5$alkyl,
(c) hydroxy,
(d) aryl,
(e) —Het,
(f) guanidinyl $C_1-C_3$alkyl-, or
(g) $-(CH_2)_p-C_3-C_7$cycloalkyl;
wherein $R_9$ is
(a) hydrogen,
(b) hydroxy,
(c) amino $C_1-C_4$alkyl-, or
(d) guanidinyl $C_1-C_3$alkyl-;
wherein $R_{10}$ is
(a) hydrogen,
(b) $C_1-C_5$alkyl,
(c) $-(CH_2)_nR_{16}$,
(d) $-(CH_2)_nR_{17}$,
(e) $C_3-C_7$cycloalkyl,
(f) a pharmaceutically acceptable cation,
(g) $-CH(R_{25})-CH_2-R_{15}$, or
(h) $-CH_2-CH(R_{12})-R_{15}$;
wherein $R_{11}$ is —R or $-R_2$;
wherein $R_{12}$ is $-(CH_2)_n-R_{13}$;
wherein $R_{13}$ is
(a) aryl,
(b) amino,
(c) mono-, di or tri-$C_1-C_3$alkylamino,
(d) —Het,
(e) $C_1-C_5$alkyl
(f) $C_3-C_7$cycloalkyl,
(g) $C_{12}-C_5$alkenyl,
(h) $C_3-C_7$cycloalkenyl,
(i) hydroxy,
(j) $C_1-C_3$alkoxy,
(k) $C_1-C_3$alkanoyloxy,
(l) mercapto,
(m) $C_1-C_3$alkylthio,
(n) —COOH,
(o) $-CO-O-C_1-C_6$alkyl,
(p) $-CO-O-CH_2-(C_1-C_3$alkyl$)-N(C_1-C_3$alkyl$)_2$,
(q) $-CO-NR_{22}R_{26}$;
(r) $C_4-C_7$cyclic amino,
(s) $C_4-C_7$cycloalkylamino,
(t) guanidyl,
(u) cyano,
(v) N-cyanoguanidyl, (w) cyanoamino,
(x) (hydroxy $C_2$-$C_4$alkyl)amino, or
(y) di-(hydroxy$C_2$-$C_4$alkyl)amino;
wherein $R_{14}$ is
(a) hydrogen,
(b) $C_1$-$C_{10}$alkyl,
(c) —$(CH_2)_n$—$R_{18}$,
(d) —$(CH_2)_n$—$R_{19}$,
(e) —$CH(R_{25})$—$CH_2$—$R_{15}$,
(f) —$CH_2$—$CH(R_{12})$—$R_{15}$,
(g) (hydroxy $C_1$-$C_8$alkyl), or
(h) ($C_1$-$C_3$alkoxy)$C_1$-$C_8$alkyl;
wherein $R_{15}$ is
(a) hydroxy,
(b) $C_3$-$C_7$cycloalkyl,
(c) aryl,
(d) amino,
(e) mono-, di-, or tri-$C_1$-$C_3$alkylamino,
(f) mono- or di-[hydroxy $C_2$-$C_4$alkyl]amino,
(g) —Het,
(h) $C_1$-$C_3$alkoxy—,
(i) $C_1$-$C_3$alkanoyloxy-,
(j) mercapto,
(k) $C_1$-$C_3$alkylthio-,
(l) $C_1$-$C_5$alkyl,
(m) $C_4$-$C_7$cyclic amino,
(n) $C_4$-$C_7$cycloalkylamino,
(o) $C_1$-$C_5$alkenyloxy,
(p) $C_3$-$C_7$cycloalkenyl;
wherein $R_{16}$ is
(a) aryl,
(b) amino,
(c) mono- or di-$C_1$-$C_3$alkylamino,
(d) hydroxy,
(e) $C_3$-$C_7$cycloalkyl,
(f) $C_4$-$C_7$cyclic amino, or
(g) $C_1$-$C_3$alkanoyloxy;
wherein $R_{17}$ is
(a) —Het,
(b) $C_1$-$C_5$alkenyl,
(c) $C_3$-$C_7$cycloalkenyl,
(d) $C_1$-$C_3$alkoxy,
(e) mercapto,
(f) $C_1$-$C_3$alkylthio,
(g) —COOH,
(h) —CO—O—$C_1$—$C_6$alkyl,
(i) —CO—O—$CH_2$—($C_1$—$C_3$alkyl)—N($C_1$—$C_3$alkyl)$_2$,
(j) —CO—$NR_{22}R_{26}$,
(k) tri-$C_1$-$C_3$alkylamino,
(l) guanidyl,
(m) cyano,
(n) N-cyanoguanidyl,
(o) (hydroxy $C_2$-$C_4$alkyl)amino,
(p) di-(hydroxy $C_2$-$C_4$alkyl)amino, or
(q) cyanoamino;
wherein $R_{18}$ is
(a) amino,
(b) mono-, or di-$C_1$-$C_3$alkylamino,
(c) $C_4$-$C_7$cyclic amino; or
(d) $C_4$-$C_7$cycloalkylamino;
wherein $R_{19}$ is
(a) aryl,
(b) —Het,
(c) tri-$C_1$-$C_3$alkylamino,
(d) $C_3$-$C_7$cycloalkyl,
(e) $C_1$-$C_5$alkenyl,
(f) $C_3$-$C_7$cycloalkenyl, (g) hydroxy,
(h) $C_1$-$C_3$alkoxy,
(i) $C_1$-$C_3$alkanoyloxy,
(j) mercapto,
(k) $C_1$-$C_3$alkylthio,
(l) —COOH,
(m) —CO—O—$C_1$—$C_6$alkyl,
(n) —CO—O—$CH_2$—($C_1$—$C_3$alkyl)—N($C_1$—$C_3$alkyl)$_2$,
(o) —CO—$NR_{22}R_{26}$,
(p) guanidyl,
(q) cyano,
(r) N-cyanoguanidyl,
(s) cyanoamino,
(t) (hydroxy $C_2$-$C_4$alkyl)amino,
(u) di-(hydroxy $C_2$-$C_4$alkyl)amino; or
(v) —$SO_3H$;
wherein $R_{20}$ is
(a) hydrogen,
(b) $C_1$-$C_5$alkyl, or
(c) aryl-$C_1$-alkyl;
wherein $R_{22}$ is
(a) hydrogen, or
(b) $C_1$-$C_3$alkyl;
wherein $R_{23}$ is
(a) —$(CH_2)_n$—OH,
(b) —$(CH_2)_n$—$NH_2$,
(c) aryl, or
(d) $C_1$-$C_3$alkyl;
wherein $R_{25}$ is
(a) hydrogen,
(b) $C_1$-$C_3$alkyl, or
(c) phenyl-$C_1$-$C_3$alkyl;
wherein $R_{26}$ is
(a) hydrogen,
(b) $C_1$-$C_3$-alkyl, or
(c) phenyl-$C_1$-$C_3$alkyl;
wherein m is one or two;
wherein for each occurrence n is independently an integer of zero to five, inclusive;
wherein p is zero to 2 inclusive;
wherein q is 1 to 5, inclusive;
wherein Q is
(a) —$CH_2$—,
(b) —CH(OH)—,
(c) —O—, or
(d) —S—; and
wherein M is
(a) —CO—, or
(b) —$CH_2$—;
wherein aryl is phenyl or naphthyl substituted by zero to 3 to the following:
(a) $C_1$-$C_3$alkyl,
(b) hydroxy,
(c) $C_1$-$C_3$alkoxy,
(d) halo,
(e) amino,
(f) mono- or di-$C_1$-$C_3$alkyamino,
(g) —CHO,
(h) —COOH,
(i) $COOR_{26}$,
(j) $CONHR_{26}$,
(k) nitro,
(l) mercapto,
(m) $C_1$-$C_3$alkylthio,
(n) $C_1$-$C_3$alkylsulfinyl,
(o) $C_1$-$C_3$alkylsulfonyl,
(p) —N($R_4$)—$C_1C_3$alkylsulfonyl, (q) SO$_3$H,
(r) SO$_2$NH$_2$,
(s) —CN, or
(t) —CH$_2$NH$_2$;
wherein —Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:
(i) C$_1$–C$_6$alkyl,
(ii) hydroxy,
(iii) trifluoromethyl,
(iv) C$_1$–C$_4$alkoxy,
(v) halo,
(vi) aryl,
(vii) aryl C$_1$–C$_4$alkyl-,
(viii) amino,
(ix) mono- or di-C$_1$C$_4$alkylamino, and
(x) C$_1$–C$_5$alkanoyl;
with the overall provisos that
(1) R$_{18}$ or R$_{19}$ is hydroxy, mercapto, or amino, or a mono-substituted nitrogen containing group bonded through the nitrogen only when n is not one;
(2) R$_{12}$ is —(CH$_2$)$_n$—R$_{13}$ and n is zero and both R$_{13}$ and R$_{15}$ are oxygen-, nitrogen-, or sulfur-containing substituents bonded through the hetero atom, only when the hetero atom is not also bonded to hydrogen;
(3) R$_{17}$ or R$_{19}$ is —COOH only when n for that moiety is other than zero;
(4) R$_{16}$ or R$_{17}$ is an amino-containing substutient, hydroxy, mercapto, or —Het bonded through the hetero atom only when n for that substuent is an integer from two to five, inclusive;
(5) when R$_{12}$ is —(CH$_2$)$_n$—R$_{13}$ and n is zero, then R$_{13}$ and R$_{15}$ cannot both be —COOH; and
(6) R$_{17}$ or R$_{19}$ is —Het, only when —Het is other than cyclic amino;
or a carboxy-, amino-, or other reactive group-protected form thereof;
or a pharmaceutically acceptable acid addition salt thereof.

2. [5S-[[(N-tert-Butyloxycarbonyl-L-phenylalanyl)-L-histidyl]amino]-3,4R-dihydroxy-2R-isopropyl-7-methyloctanoyl]-L-isoleucyl-2-pyridylmethylamide) (also named Boc-Phe-His-LVDA-Ile-AMP), a compound of claim 1.

3. A compound of claim 1, selected from the group consisting of:
[5S-[(1'-Naphthoxyacetyl)-L-histidyl]amino-3R,4R-dihydroxy-2R-isopropyl-7-methyloctanoyl]-L-isoleucyl-2-pyridylmethylamide;
[5S-(Phenoxyacetyl-L-histidyl)amino-3R,4R-dihydroxy-2R-isopropyl-7-methyloctanoyl]-L-isoleucyl-2-pyridylmethylamide;
[5S-(Phenoxyacetyl-L-histidyl)amino-3R,4R-dihydroxy-2R-isopropyl-7-methyloctanoyl]-2S-methylbutylamide;
[5S-[(1'-Naphthoxyacetyl)-L-histidyl]amino-3R,4R-dihydroxy-2R-isopropyl-7-methyloctanoyl]-2S-methylbutylamide;
[5S-[[(N-tert-Butyloxycarbonyl-L-phenylalanyl)-L-histidyl]amino]-3R,4R-dihydroxy-2R-isopropyl-7-methyloctanoyl]-2S-methylbutylamide;
[5S-[[(N-tert-Butyloxycarbonyl-L-phenylalanyl)-(N$^\alpha$-methyl-L-histidyl)]amino-3R,4R-dihydroxy-2R-isopropyl-7-methyloctanoyl]-L-isoleucyl-2-pyridylmethylamide;
[5S-[[(N-tert-Butyloxycarbonyl-L-propyl)-L-phenylalanyl-(N$^\alpha$-methyl-L-histidyl)]amino]-3R,4R-dihydroxy-2R-isopropyl-7-methyloctanoyl]-L-isoleucyl-2-pyridylmethylamide;
[5S-[[(N-tert-butyloxycarbonyl-L-phenylalanyl)-L-histidyl]amino]-6-cyclohexyl-3R,4R-dihydroxy-2R-isopropylhexanoyl]-L-isoleucyl-2-pyridylmethylamide;
[5S-[[(N-tert-Butyloxycarbonyl-L-phenylalanyl)-(N$^\alpha$-methyl-L-histidyl)]amino]-6-cyclohexyl-3R,4R-dihydroxy-2R-isopropylhexanoyl]-L-isoleucyl-2-pyridylmethylamide;
[5S-[[(N-Acetyl-L-prolyl)-L-phenylalanyl-(N$^\alpha$-methyl-L-histidyl)]amino]-6-cyclohexyl-3R,4R-dihydroxy-2R-isopropylhexanoyl]-L-isoleucyl-2-pyridylmethylamide;
[5S-[(1'-Naphthoxyacetyl)-L-histidyl]amino-6-cyclohexyl-3R,4R-dihydroxy-2R-isopropylhexanoyl]-L-isoleucyl-2-pyridylmethylamide; and
[5S-[[(N-Acetyl-L-prolyl)-L-phenylalanyl-(N$^\alpha$-methyl-L-histidyl)]amino]-3R,4R-dihydroxy-2R-isopropyl-7-methyloctanoyl]-L-isoleucyl-2-pyridylmethylamide.

* * * * *

UNITED STATES PATENT AND TRADEMARK OFFICE
CERTIFICATE OF CORRECTION

PATENT NO. : 4,864,017

DATED : September 5, 1989

INVENTOR(S) : Suvit Thaisrivongs

Page 1 of 5

It is certified that error appears in the above-indentified patent and that said Letters Patent is hereby corrected as shown below:

Column 1, line 59, "an isotere bond." should read -- an isostere bond. --

Column 2, line 59, "R os S" should read -- R or S --

Column 3, line 51 "$C_1$-alkyl" should read -- $C_1$-$C_4$ alkyl --

Column 5, line 58 "$C_1$-alkyl" should read -- $C_1$-$C_5$ alkyl --

Column 6, line 27 "alkyamino," should read -- alkylamino, --

Column 7, line 33, "glycerophasphate," should read -- glycerophosphate, --

Column 8, line 14, "thenyl, and" should read -- thienyl, and --

Column 8, line 17 "chemistry, heterocycle" should read -- chemistry, a heterocycle --

Column 8, line 24, "pharmaceutically" should read -- pharmacologically --

Column 8, line 25, "quanternary" should read -- quaternary --

Column 9, line 37 "102:5974 (2980)" should read -- 102:5974 (1980) --

Column 9, line 57 "butylocycarbonyl" should read -- butyloxycarbonyl --

Column 9, line 63 "12 to the" should read -- 12 according to the --

Column 11, line 5, "Biochem." should read -- Biochim. --

Column 11, lines 58-59 "3-cycloxylalanyl," should read -- 3-cyclohexylalanyl --

Column 12, line 19 "MOA1 is" should read -- NOA1 is --

Column 12, line 36 "relative to the place" should read -- relative to the plane --

Column 12, line 39, "the plant of the paper" should read -- the plane of the paper --

Column 12, line 39 "relative to the place" should read -- relative to the plane --

Column 12, lines 60-61, "Evaporated" should read -- Evaporative --

UNITED STATES PATENT AND TRADEMARK OFFICE
CERTIFICATE OF CORRECTION

PATENT NO. : 4,864,017
DATED : September 5, 1989
INVENTOR(S) : Suvit Thaisrivongs It is certified that error appears in the above-indentified patent and that said Letters Patent is hereby corrected as shown below:

Column 13, line 10, "Evaporated" should read -- Evaporative --

Column 13, line 52 "($M^--CH_3$)" should read -- ($M^+-CH_3$) --

Column 13, lines 59-60 "acetonitrole" should read -- acetonitrile --

Column 14, lines 18-19 "(4.50 mmol)" should read -- (4.59 mmol) --

Column 14, line 21 "the reaction" should read -- the reaction mixture --

Column 14, line 29 "desired epoxy amide" should read -- desired titled epoxy amide --

Column 15, line 50 "oxazolininecarboxaldehyde" should read -- oxazolidinecarboxaldehyde --

Column 15, line 58 "MaOH." should read -- NaOH.--

Column 16, lines 5-6 "dry dichloromathane" should read -- dry dichloromethane --

Column 16, line 18 "and 9.59." should read -- and 9.58. --

Column 16, line 21 "-3R-ol" should read -- -3RS-ol --

Column 16, line 67 "and 7.5" should read -- and 7.5 ml --

Column 17, line 6 "dichloromathane" should read -- dichloromethane --

Column 17, line 30 "affords 221 g" should read -- affords 2.21 g --

Column 17, line 32 "9.92." should read -- 9.82. --

Column 17, line 40 "(35.09 mmol)" should read -- (35.79 mmol) --

Column 17, line 48 "with 30" should read -- with 30 ml --

Column 17, line 50 "Evaporated" should read -- Evaporative --

Column 17, line 54 "0.97, 2.12," should read -- 0.97, 0.98, 2.12, --

Column 20, line 23 "vigoriously" should read -- vigorously --

Column 20, line 33 "0.01, 0.76," should read -- 0.02, 0.76, --

UNITED STATES PATENT AND TRADEMARK OFFICE
CERTIFICATE OF CORRECTION

PATENT NO. : 4,864,017
DATED : September 5, 1989
INVENTOR(S) : Suvit Thaisrivongs It is certified that error appears in the above-indentified patent and that said Letters Patent is hereby corrected as shown below:

Column 21, line 15 "(MGSO$_4$)" should read -- (MgSO$_4$)

Column 21, line 40 "NAHCO$_3$" should read -- NaHCO$_3$ --

Column 21, line 50 "Bormide" should read -- bromide --

Column 22, line 24 "244.1989" should read -- 244.1898 --

Column 23, line 5 "[M+H]" should read -- [M+H]$^+$ --

Column 23, line 12 "dioxoland" should read -- dioxolane --

Column 23, line 18 "C, 64,65;" should read -- C, 64.65; --

Column 23, line 50 "dichloromathane" should read -- dichloromethane --

Column 24, line 25 "2pyridylmethylamide" should read -- 2-pyridylmethylamide --

Column 24, line 29 "0.5 of" should read -- 0.5 ml of --

Column 25, line 21 "]amino-3R" should read -- ]amino]-3R --

Column 25, line 26 "L-propyl)" should read -- L-prolyl) --

Column 25, line 52 "isopropylhexanolyl" should read -- isopropylhexanoyl] --

Column 26, line 26, at structure 6 reading

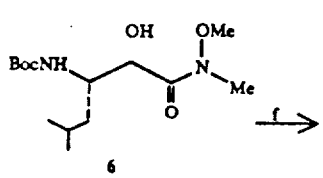 should read 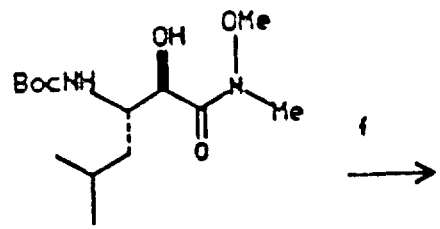

UNITED STATES PATENT AND TRADEMARK OFFICE
CERTIFICATE OF CORRECTION

PATENT NO. : 4,864,017
DATED : September 5, 1989
INVENTOR(S) : Suvit Thaisrivongs It is certified that error appears in the above-indentified patent and that said Letters Patent is hereby corrected as shown below:

Column 27, at structure 13 reading

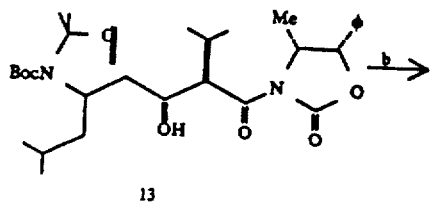   should read   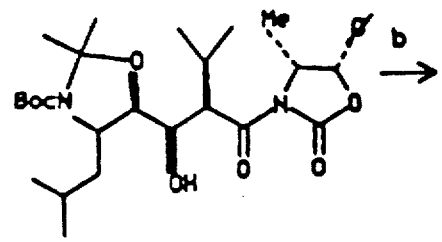

Column 27, at structure 14 reading

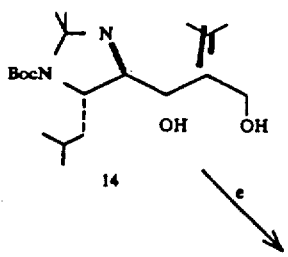   should read   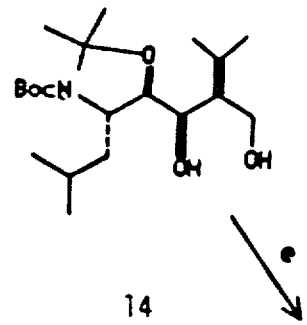

Column 27, line 38 "(b) nBu$_3$B;" should read -- (b) nBu$_3$B, HOAc; --
Column 27, line 39 "(d) K$_2$CO$_3$; RuCl$_3$," should read -- (d) K$_2$CO$_3$, CH$_3$OH; RuCl$_3$, --
Column 29, line 45 "(CH$_2$)$_i$-" should read -- (CH$_2$)- --

UNITED STATES PATENT AND TRADEMARK OFFICE
CERTIFICATE OF CORRECTION

PATENT NO. : 4,864,017
DATED : September 5, 1989
INVENTOR(S) : Suvit Thaisrivongs It is certified that error appears in the above-indentified patent and that said Letters Patent is hereby corrected as shown below:

Column 30, line 20 at Structure $XL_2$ reading

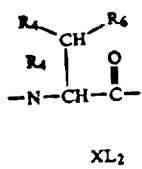     should read     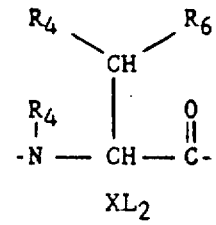

Column 32, line 14 "$C_1$-alkyl" should read -- $C_1$-$C_4$ alkyl --

Column 35, line 36 "substuent" should read -- substituent --
Column 35, line 48 "methylamide)" should read -- methylamide --
Column 36, line 21 "]amino-3R" should read -- ]amino]-3R --
Column 36, line 24 "L-propyl)-" should read -- L-prolyl)- --

Signed and Sealed this

First Day of February, 1994

Attest:

BRUCE LEHMAN

*Attesting Officer*    Commissioner of Patents and Trademarks